(12) United States Patent
Yukawa et al.

(10) Patent No.: US 9,453,248 B2
(45) Date of Patent: Sep. 27, 2016

(54) CORYNEFORM BACTERIUM TRANSFORMANT AND PROCESS FOR PRODUCING ANILINE USING THE SAME

(71) Applicants: RESEARCH INSTITUTE OF INNOVATIVE TECHNOLOGY FOR THE EARTH, Kyoto (JP); SUMITOMO RUBBER INDUSTRIES, LTD., Hyogo (JP)

(72) Inventors: Hideaki Yukawa, Kyoto (JP); Masayuki Inui, Kyoto (JP)

(73) Assignees: RESEARCH INSTITUTE OF INNOVATIVE TECHNOLOGY FOR THE EARTH, Kyoto (JP); SUMITOMO RUBBER INDUSTRIES, LTD., Hyogo (JP)

( * ) Notice: Subject to any disclaimer, the term of this patent is extended or adjusted under 35 U.S.C. 154(b) by 0 days.

(21) Appl. No.: 14/983,178

(22) Filed: Dec. 29, 2015

(65) Prior Publication Data

US 2016/0130617 A1 May 12, 2016

Related U.S. Application Data

(63) Continuation of application No. 13/997,107, filed as application No. PCT/JP2011/080151 on Dec. 27, 2011, now abandoned.

(30) Foreign Application Priority Data

Dec. 28, 2010 (JP) ................. 2010-293972

(51) Int. Cl.
*C12P 13/00* (2006.01)
*C12N 9/88* (2006.01)
*C12N 15/77* (2006.01)

(52) U.S. Cl.
CPC ............... *C12P 13/001* (2013.01); *C12N 9/88* (2013.01); *C12N 15/77* (2013.01); *C12Y 401/01024* (2013.01); *Y02P 20/52* (2015.11)

(58) Field of Classification Search
None
See application file for complete search history.

(56) References Cited

U.S. PATENT DOCUMENTS

2008/0242823 A1  10/2008  Fujikura
2013/0273624 A1  10/2013  Yukawa et al.

FOREIGN PATENT DOCUMENTS

| JP | 2006-050914 A | 2/2006 |
| JP | 2008274225 A | 11/2008 |
| WO | WO-2011050326 A1 | 4/2011 |
| WO | WO-2012063862 A1 | 5/2012 |

OTHER PUBLICATIONS

Kagaku to Kyoiku (Chemistry and Education) 39(5), 1991, "Synthesis of Bio-Aniline".
Kahng et al., "Characterization of strain HY99, a novel microorganism capable of aerobic and anaerobic degradation of aniline", Feb. 2, 2000.
Lupa et al., "Properties of the reversible nonoxidative vanillate/4-hydroxybenzoate decarboxylase from Bacillus subtilis", Jun. 29, 2007.
Matsui et al., "Purification, characterization, and gene cloning of 4-hydroxybenzoate decarboxylase of Enterobacter cloacae P240", Oct. 23, 2005.
McCullough et al., "Enzymatic Decarboxylation of the Aminobenzoates", Jul. 19, 1956.
Nelson et al., "Complete genome sequence and comparative analysis of the metabolically versatile Pseudomonas putida KT2440", Oct. 10, 2002.
Sloane et al., "Studies on the Metabolism of p-Aminobenzoic Acid by *Mycobacterium Smegmatis*", Apr. 3, 1951.
Stetz et al., "The ADE2 gene from *Saccharomyces cerevisiae*: sequence and new vectors", Apr. 18, 1990.
Tiedeman et al., "Nucleotide Sequence Analysis of the purEK Operon Encoding,,,", Oct. 3, 1988.
International Preliminary Report on Patentability and Written Opinion (English and Japanese) of PCT/JP2011/080151, dated Jul. 10, 2013.
International Search Report in corresponding PCT/JP2022/080151 dated Mar. 27, 2012.
Database Accession No. GSN: AEJ52762.
N.H. Sloane et al., "Metabolites of p-Aminobenzoic Acid," *Biochim. Biophys. Acta*, pp. 588-593 (1963).
Database Accession No. GSN: AZW45541.
Extended European Search Report for PCT/JP2011/080151 dated Apr. 22, 2014.
Yukawa et al., Comparative analysis of the Corynebacterium glutamicum group and complete genome sequence of strain R. 2007. Microbiology. 153, p. 1042-1058.
International Search Report in corresponding PCT/JP2011/080151 dated Mar. 27, 2012.

*Primary Examiner* — Paul Holland
(74) *Attorney, Agent, or Firm* — Marshall, Gerstein & Borun LLP

(57) ABSTRACT

Provided is an aniline-producing transformant constructed by introducing a gene which encodes an enzyme having aminobenzoate decarboxylase activity into a coryneform bacterium as a host. Also provided is a process for producing aniline, which comprises a step of allowing the transformant to react in a reaction mixture containing aminobenzoic acid, an ester thereof, and/or a salt thereof under reducing conditions, and a step of recovering aniline from the reaction mixture.

6 Claims, 1 Drawing Sheet

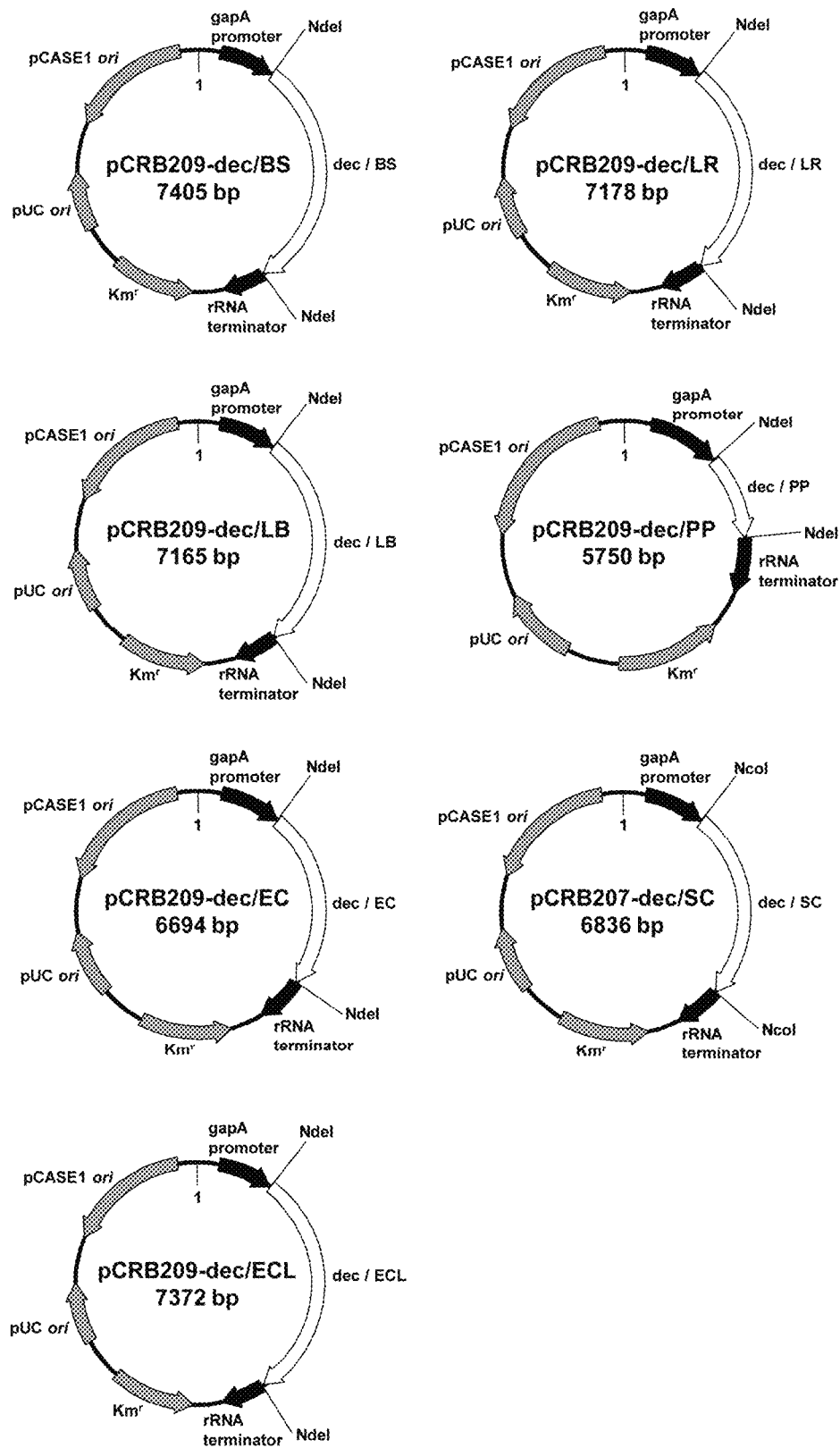

CORYNEFORM BACTERIUM TRANSFORMANT AND PROCESS FOR PRODUCING ANILINE USING THE SAME

CROSS-REFERNECE TO RELATED APPLICATIONS

This application is a continuation of U.S. application Ser. No. 13/997,107 filed Jul. 30, 2013, now abandoned, which is a U.S. National Stage of PCT/JP2011/080151 filed Dec. 27, 2011, which claims priority to JP 2010-293972, filed Dec. 28, 2010, the disclosures of which are incorporated herein by reference in their entireties.

INCORPORATIOIN BY REFERNECE OF MATERIAL SUBMITTED ELECTRONICALLY

Incorporated by reference in its entirety is a computer-readable sequence listing submitted concurrently herewith and identified as follows:
Filename: 47707A_SeqListing.txt, 35,785 bytes, created Dec. 29, 2015.

TECHNICAL FIELD

The present invention relates to a technique for producing aniline. In more detail, the present invention relates to a coryneform bacterium transformant constructed by specific gene recombination and thereby provided with an aniline-producing function, and relates to an efficient aniline-producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

Aniline is widely used as raw materials for various products including chemical products, such as dyes and rubber product materials (a vulcanization accelerator and an antioxidant for tires, etc.); functional materials, such as and textiles and conductive polymers; agricultural chemicals; medicinal drugs; or the like.

Currently, aniline is chemically produced from crude oil as a raw material. Chemical processes for producing aniline include a process in which nitrobenzen is reduced with the use of tin or iron and hydrochloric acid; a process in which nitrobenzen is reduced by hydrogen addition with the use of a metal catalyst, such as copper or nickel; and a process called ammonolysis, in which chlorobenzene and ammonia are made to react at high temperature and pressure. They are all typical energy-consumptive processes in the chemical industry requiring great amounts of solvent and thermal energy. Therefore, in the light of global environment conservation and greenhouse gas reduction, there is an urgent need to develop an environment-conscious, energy saving process that allows production of aniline from renewable resources and can reduce carbon dioxide emissions and waste products, that is, to establish bioaniline production technologies.

However, production of bioaniline from renewable resources is less productive as compared to production of lactic acid or ethanol because the metabolic reaction from a raw material sugar consists of a great many steps. In addition, there are problems, such as inhibition of bacterial growth by produced aniline and cytotoxicity of aniline. Therefore, industrial production of aniline has been considered to be impossible.

Specifically known examples of technologies for producing aniline are as follows.

For example, Non Patent Literature 1 discloses that a slight amount of aniline is produced by culturing *Mycobacterium smegmatis*, washing the cells, and then adding 4-aminobenzoic acid. However, the process of Non Patent Literature 1 does not show practically sufficient aniline productivity. Non Patent Literature 1 does not mention any enzyme involved in aniline production from 4-aminobenzoic acid, let alone its activity or related gene.

Non Patent Literature 2 discloses that a slight amount of aniline is produced by adding anthranilic acid (2-aminobenzoic acid) or 4-aminobenzoic acid to washed cells of virulent *Escherichia coli* O111 or an extract from the cells. However, the process of Non Patent Literature 2 does not have practically sufficient aniline productivity. Non Patent Literature 2 does not mention any enzyme involved in aniline production from 4-aminobenzoic acid, let alone its activity or related gene.

Patent Literature 1 discloses a technology in which *Streptomyces griseus* is cultured in TSB culture medium (Trypticase Soy Broth) supplemented with glucose (raw material for aniline) under aerobic conditions for 4 to 5 days for aniline production. However, Patent Literature 1 does not specifically show the amount of produced aniline or the productivity. Therefore, the practicality of the method of Patent Literature 1 is unknown.

CITATION LIST

Patent Literature

[PTL 1] JP 2008-274225 A

Non Patent Literature

[NPL 1] The Journal of Biological Chemistry, Vol. 193, 1951, 453-458.
[NPL 2] Journal of the American Chemical Society, Vol. 79, 1957, 628-630.

SUMMARY OF INVENTION

Technical Problem

An object of the present invention is to provide a microorganism capable of efficiently producing aniline from aminobenzoic acid, and a process for efficiently producing aniline from aminobenzoic acid.

Solution to Problem

The present inventors have wholeheartedly carried out investigations in order to achieve the object described above and obtained the findings that a transformant constructed by introducing an aminobenzoate decarboxylase gene into a coryneform bacterium can efficiently produce aniline from aminobenzoic acid and that the transformant has a particularly higher aniline productivity when growth is substantially inhibited in a reaction mixture under reducing conditions.

The present invention, which has been completed based on the above-mentioned findings, provides the following transformant and process for producing aniline.

[1] An aniline-producing transformant constructed by introducing a gene which encodes an enzyme having aminobenzoate decarboxylase activity into a coryneform bacterium as a host.

[2] The transformant of the above [1], wherein the gene which encodes an enzyme having aminobenzoate decarboxylase activity is a gene derived from *Bacillus subtilis*, a gene derived from *Lactobacillus rhamnosus*, a gene derived from *Lactobacillus brevis*, a gene derived from *Pseudomonas putida*, a gene derived from *Escherichia coli*, a gene derived from *Saccharomyces cerevisiae*, or a gene derived from *Enterobacter cloacae*.

[3] The transformant of the above [1], wherein the gene which encodes an enzyme having aminobenzoate decarboxylase activity is the DNA of the following (a) or (b).

(a) a DNA consisting of the base sequence of SEQ ID NO: 16, SEQ ID NO: 19, SEQ ID NO: 22, SEQ ID NO: 25, SEQ ID NO: 28, SEQ ID NO: 31, or SEQ ID NO: 34

(b) a DNA which hybridizes to a DNA consisting of a complementary base sequence of any of the DNAs of (a) under stringent conditions and which encodes a polypeptide having aminobenzoate decarboxylase activity

[4] The transformant of any one of the above [1] to [3], wherein the coryneform bacterium as the host is *Corynebacterium glutamicum*.

[5] The transformant of the above [4], wherein the coryneform bacterium as the host is *Corynebacterium glutamicum* R (FERM BP-18976), ATCC13032, or ATCC13869.

[6] *Corynebacterium glutamicum* ANI-1 (Accession Number: NITE BP-1001), which is a transformant of *Corynebacterium glutamicum*.

[7] A process for producing aniline, which comprises a step of allowing the transformant of any one of the above [1] to [6] to react in a reaction mixture containing aminobenzoic acid, an ester thereof, and/or a salt thereof under reducing conditions, and a step of recovering aniline from the reaction mixture.

[8] The process of the above [7], wherein the transformant does not substantially grow in the reaction step.

[9] The process of the above [7] or [8], wherein the oxidation-reduction potential of the reaction mixture under reducing conditions is −200 mV to −500 mV.

Advantageous Effects of Invention

With the use of the transformant of the present invention, aniline can be efficiently produced from aminobenzoic acid, a salt thereof, and/or an ester thereof.

Generally, growth of microorganisms is inhibited by a solvent, such as aniline, because of its cytotoxicity, and therefore aniline production with the use of microorganisms has been difficult. According to the process of the present invention, however, aniline production with the use of microorganisms can be achieved with a practically sufficient efficiency.

BRIEF DESCRIPTION OF DRAWINGS

FIG. 1 shows the constructs of plasmids used in Examples.

DESCRIPTION OF EMBODIMENTS

Hereinafter, the present invention will be described in detail.

(I) Aniline-Producing Transformant

The transformant of the present invention capable of producing aniline is a transformant constructed by introducing a gene which encodes an enzyme having aminobenzoate decarboxylase activity into a coryneform bacterium as a host.

Host

The coryneform bacterium is a group of microorganisms defined in Bergey's Manual of Determinative Bacteriology, Vol. 8, 599 (1974), and is not particularly limited as long as it grows under normal aerobic conditions.

The specific examples include *Corynebacterium*, *Brevibacterium*, *Arthrobacter*, *Mycobacterium* and *Micrococcus*. Among the coryneform bacteria, *Corynebacterium* is preferred.

Examples of the *Corynebacterium* include *Corynebacterium glutamicum*, *Corynebacterium efficiens*, *Corynebacterium ammoniagenes*, *Corynebacterium halotolerance*, and *Corynebacterium alkanolyticum*.

Inter alia, *Corynebacterium glutamicum* is preferred for safety and high aniline production. Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, strains R (FERM P-18976), ATCC13032, and ATCC13869 are preferred.

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)).

*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.

Examples of the *Brevibacterium* include *Brevibacterium ammoniagenes* (for example, ATCC6872).

Examples of the *Arthrobacter* include *Arthrobacter globiformis* (for example, ATCC8010, ATCC4336, ATCC21056, ATCC31250, ATCC31738 and ATCC35698).

Examples of the *Mycobacterium* include *Mycobacterium bovis* (for example, ATCC19210 and ATCC27289).

Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve aniline productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, especially preferred is a disruptant of *Corynebacterium glutamicum* R (FERM P-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1.

Compared with other bacteria, coryneform bacteria are more resistant to solvents, such as aniline. Further, compared with other aerobic bacteria, coryneform bacteria more efficiently produce substances under reducing conditions where growth is substantially inhibited. In these respects, coryneform bacteria are suitable for the aniline production by the method of the present invention.

Aminobenzoate Decarboxylase Gene

Aminobenzoate decarboxylase is an enzyme that catalyzes a reaction in which aniline is produced by elimination of carbonic acid from aminobenzoic acid and the reverse reaction.

The gene which encodes an enzyme having aminobenzoate decarboxylase activity may be of any origin without particular limitation, and preferred examples thereof include a gene derived from *Bacillus subtilis*, a gene derived from *Lactobacillus rhamnosus*, a gene derived from *Lactobacillus brevis*, a gene derived from *Pseudomonas putida*, a gene derived from *Escherichia coli*, a gene derived from *Saccharomyces cerevisiae*, and a gene derived from *Enterobacter cloacae*. Inter alia, more preferred are a gene derived from *Bacillus subtilis* and a gene derived from *Enterobacter cloacae*. In particular, when the substrate is anthranilic acid (2-aminobenzoic acid), preferred is a gene derived from *Bacillus subtilis*, and when the substrate is 4-aminobenzoic acid, preferred is a gene derived from *Enterobacter cloacae*.

Examples of the gene derived from *Bacillus subtilis* include the DNA consisting of the base sequence of SEQ ID NO: 16, examples of the gene derived from *Lactobacillus rhamnosus* include the DNA consisting of the base sequence of SEQ ID NO: 19, examples of the gene derived from *Lactobacillus brevis* include the DNA consisting of the base sequence of SEQ ID NO: 22, examples of the gene derived from *Pseudomonas putida* include the DNA consisting of the base sequence of SEQ ID NO: 25, examples of the gene derived from *Escherichia coli* include the DNA consisting of the base sequence of SEQ ID NO: 28, examples of the gene derived from *Saccharomyces cerevisiae* include the DNA consisting of the base sequence of SEQ ID NO: 31, and examples of the gene derived from *Enterobacter cloacae* include the DNA consisting of the base sequence of SEQ ID NO: 34.

In the present invention, a DNA which hybridizes to a DNA consisting of a complementary base sequence of the base sequence of SEQ ID NO: 16, 19, 22, 25, 28, 31, or 34 under stringent conditions and which encodes a polypeptide having aminobenzoate decarboxylase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

The aminobenzoate decarboxylase activity can be measured by a modified method of the method described in J. Am. Chem. Soc., 79, 628-630 (1957). Briefly, a coryneform bacterium is cultured in a nutrient medium at 33° C. for 18 hours, washed with minimal medium twice, and resuspended in minimal medium to prepare intact cells. Subsequently, for the reaction, HEPES (pH 7.0) as a buffer solution is added to the intact cells so that the concentration is 25 mM, and anthranilic acid or 4-amino benzoate as a substrate is added so that the final concentration is 5 mM. After shaking at 200 rpm at 33° C. for 6 hours, the reaction mixture was centrifuged to separate bacterial cells and supernatant. The supernatant is filtered through a 0.22-µm filter, and the filtrate is used as a sample. The produced aniline can be quantified by GC/MS or HPLC.

In the present invention, a DNA consisting of a base sequence which has 90% or more, preferably 95% or more, more preferably 98% or more homology with the base sequence of SEQ ID NO: 16, 19, 22, 25, 28, 31, or 34 and which encodes a polypeptide having aminobenzoate decarboxylase activity can also be used.

The base sequence homology was calculated using GENETYX Ver. 8 (made by Genetyx).

The homologue of the DNA consisting of the base sequence of SEQ ID NO: 16, 19, 22, 25, 28, 31, or 34 can be selected from a DNA library of a different species by, for example, PCR or hybridization using a primer or a probe designed based on these base sequences, according to a conventional method, and as a result, a DNA which encodes a polypeptide having aminobenzoate decarboxylase activity can be obtained with a high probability.

Construction of Vector for Transformation

The DNA which encodes aminobenzoate decarboxylase is amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799A; and Katsumata, R. et al., Protoplast transformation of glutamate-producing bacteria with plasmid DNA. J. Bacteriol., 159: 306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum*/*Escherichia coli* shuttle vectors for cloning, controlled gene expression, and promoter probing. Gene, 102:93-98 (1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for a coryneform bacterium is electroporation, which can be performed by a known method (Kurusu, Y. et al., Electroporation-transformation system for Coryneform bacteria by auxotrophic complementation, Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

(II) Process for Producing Aniline

Aniline can be produced by a process comprising a step of allowing the above-described transformant of the present invention to react in a reaction mixture containing aminobenzoic acid, a salt thereof, and/or an ester thereof, and a step of recovering aniline from the reaction mixture.

Growth of Microorganism

Before the reaction, the transformant is preferably cultured and grown under aerobic conditions at about 25 to 35° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

As the reaction mixture, water, a buffer solution, an inorganic salt medium, or the like, containing an aniline precursor (raw material for aniline) can be used.

As the precursor, aminobenzoic acid, a salt thereof, and/or an ester thereof may be used. As the aminobenzoic acid, 2-aminobenzoic acid (o-aminobenzoic acid; anthranilic acid), 3-aminobenzoic acid (m-aminobenzoic acid), and 4-aminobenzoic acid (p-aminobenzoic acid) are all usable. Inter alia, preferred are 2-aminobenzoic acid and 4-aminobenzoic acid because they are soluble in water and thus easy to use for the reaction.

Examples of the salt include a sodium salt, a potassium salt, and a hydrochloride. Examples of the ester include esters with alcohols having 1 to 4 carbon atoms.

Salts are preferred because they are highly soluble in the reaction mixture. These precursors may be used alone or a mixture of two or more kinds.

The concentration of aminobenzoic acid, a salt thereof, and/or an ester thereof in the reaction mixture is preferably about 0.1 to 10 w/v %, more preferably about 0.5 to 7 w/v %, and still more preferably about 0.5 to 5 w/v %. When the concentration is in the above range, aniline can be efficiently produced.

Examples of the buffer solution include a phosphate buffer, a Tris buffer, a carbonate buffer, etc. The concentration of the buffer solution is preferably about 10 to 150 mM.

Examples of the inorganic salt medium include a medium containing one or more kinds of inorganic salts including potassium dihydrogen phosphate, dipotassium hydrogenphosphate, magnesium sulfate, sodium chloride, iron(II) nitrate, manganese sulfate, zinc sulfate, cobalt sulfate, and calcium carbonate. Inter alia, preferred is a medium containing magnesium sulfate. Specific example of the inorganic salt medium include BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc. The concentration of the inorganic salts in the culture medium varies depending on the kind of the inorganic salts, but is usually about 0.01 to 1 w/v %.

The pH of the reaction mixture is preferably about 6 to 8. During the reaction, the pH of the reaction mixture is preferably kept nearly neutral, in particular at around 7 with the use of aqueous ammonia, aqueous sodium hydroxide, or the like, under the control of a pH controller (for example, Type: DT-1023 made by Able).

Reaction Conditions

The reaction temperature, that is, the temperature for keeping the transformant alive during the reaction is preferably about 20 to 40° C., and more preferably about 25 to 35° C. When the temperature is in the above range, aniline can be efficiently produced.

The reaction period is preferably about 1 to 7 days, and more preferably about 1 to 3 days.

The culture may be a batch process, a fed-batch process, or a continuous process. Inter alia, a batch process is preferred.

<Reducing Conditions>

The reaction may be performed under aerobic conditions or reducing conditions, but preferably is performed under reducing conditions. Under reducing conditions, coryneform bacteria do not substantially grow and can further efficiently produce aniline.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of Aniline

Through the culture performed in the above manner, aniline is produced in the reaction mixture. Aniline can be recovered by collecting the reaction mixture, and it is also feasible to isolate aniline from the reaction mixture by a known method. Examples of such a known method include distillation, the membrane permeation method, and the organic solvent extraction method.

EXAMPLES

Hereinafter, the present invention will be described in more detail by way of Examples, but the present invention is not limited thereto.

Example 1

Cloning and Expression of Aniline-Producing Genes (1) Extraction of Chromosomal DNA from Microorganisms To extract chromosomal DNA from *Bacillus subtilis* NBRC14144, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Lactobacillus rhamnosus* NBRC3425, the bacterium was inoculated into NBRC Medium No. 804 (5 g of polypeptone, 5 g of yeast extract, 5 g of glucose, and 1 g of $MgSO_4.7H_2O$ were dissolved in 1 L of distilled water) with the use of a platinum loop, and cultured with shaking at 30° C. until the logarithmic growth phase. After bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Lactobacillus brevis* ATCC367, the bacterium was inoculated in Lactobacilli MRS broth (made by Becton, Dickinson and Company, BD 288130) with use of a platinum loop, and cultured with shaking at 30° C. until logarithmic growth phase. After bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pseudomonas putida* (KT2440) ATCC47054, the bacterium was inoculated into LB Medium (10 g of tryptone, 5 g of yeast extract, and 5 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Escherichia coli* (K-12 MG1655), the bacterium was inoculated into LB Medium (10 g of tryptone, 5 g of yeast extract, and 5 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Saccharomyces cerevisiae* NBRC10217, the bacterium was inoculated into NBRC Medium No. 108 (10 g of glucose, 5 g of polypeptone, 3 g of yeast extract, and 3 g of malt extract were dissolved in 1 L of distilled water) with the use of a platinum loop, and cultured with shaking at 24° C. until the logarithmic growth phase. After bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Enterobacter cloacae* NBRC13535, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

(2) Construction of Cloning Vectors

Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-Ori Sequence Amplification

```
(a-1);
                                    (SEQ ID NO: 3)
5'-AT AGATCT AGAACGTCCGTAGGAGC-3'

(b-1);
                                    (SEQ ID NO: 4)
5'-AT AGATCT GACTTGGTTACGATGGAC-3'
```

Primers (a-1) and (b-1) each have a BglII restriction enzyme site added thereto.

Primers for Cloning Vector pHSG298 Amplification

```
(a-2):
                                    (SEQ ID NO: 5)
5'-AT AGATCT AGGTTTCCCGACTGGAAAG-3'

(b-2):
                                    (SEQ ID NO: 6)
5'-AT AGATCT CGTGCCAGCTGCATTAATGA-3'
```

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.

*) For amplification of the pCASE1-ori sequence, a combination of primers (a-1) and (b-1), and for amplification of the cloning vector pHSG298, a combination of primers (a-2) and (b-2) were used.

PCR Cycle:
  Denaturation step: 94° C., 60 seconds
  Annealing step: 52° C., 60 seconds
  Extension step: 72° C.
  pCASE1-ori sequence: 150 seconds
  Cloning vector pHSG298: 180 seconds A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 μL of the about 1.4-kb DNA fragment comprising the pCASE1-ori sequence derived from *Corynebacterium casei*, and 10 μL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

With the use of the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 7 (PgapA sequence) and SEQ ID NO: 8 (terminator sequence) for cloning of the PgapA sequence and the terminator sequence, and were used.

Primers for PgapA Sequence Amplification (a-3);
               (SEQ ID NO: 9)
5'-CTCT <u>GTCGAC</u> CCGAAGATCTGAAGATTCCTG-3'

(b-3);
               (SEQ ID NO: 10)
5'-CTCT <u>GTCGAC</u> <u>GGATCC</u> <u>CCATGG</u>

TGTGTCTCCTCTAAAGATTGTAGG-3'

Primer (a-3) has a SalI restriction enzyme site added thereto, and primer (b-3) has SalI, BamHI, and NcoI restriction enzyme sites added thereto.

Primers for Terminator Sequence Amplification (a-4);
               (SEQ ID NO: 11)
5'-CTCT <u>GCATGC</u> <u>CCATGG</u> CTGTTTTGGCGGATGAGAGA-3'

(b-4);
               (SEQ ID NO: 12)
5'-CTCT <u>GCATGC</u> <u>TCATGA</u> AAGAGTTTGTAGAAACGCAAA

AAGG-3'

Primer (a-4) has SphI and NcoI restriction enzyme sites added thereto, and primer (b-4) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.

*) For amplification of the PgapA sequence, a combination of primers (a-3) and (b-3), and for amplification of the terminator sequence, a combination of primers (a-4) and (b-4) were used.

PCR Cycle:
  Denaturation step: 94° C., 60 seconds
  Annealing step: 52° C., 60 seconds
  Extension step: 72° C.
  PgapA sequence: 45 seconds
  Terminator sequence: 30 seconds A cycle consisting of the above 3 steps was repeated 30 times.

Using 10 μL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 μL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid B.

With the use of the Ligation Liquid B, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 μL of the about 0.4-kb DNA fragment comprising the terminator sequence derived from the plasmid pKK223-3, which was amplified by the above PCR, was cut with the use of restriction enzymes NcoI and BspHI, 2 μL of the above cloning vector pCRB206 was cut with the use of restriction enzyme NcoI, and both were processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid C.

With the use of the Ligation Liquid C, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 13 (pCRB207) for cloning of the pCRB207 sequence, and was used.

Primers for pCRB207 Sequence Amplification (a-5);
(SEQ ID NO: 14)
5'-CTCT CATATG CTGTTTTGGCGGATGAGAG-3'

(b-5);
(SEQ ID NO: 15)
5'-CTCT CATATG GTGTCTCCTCTAAAGATTGTAGG-3'

Primers (a-5) and (b-5) each have an NdeI restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.

*) For amplification of the pCRB207 sequence, a combination of primers (a-5) and (b-5) was used.

PCR Cycle:
  Denaturation step: 94° C., 60 seconds
  Annealing step: 52° C., 60 seconds
  Extension step: 72° C., 307 seconds A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut with the use of restriction enzyme NdeI and processed at 70° C. for 10 minutes for deactivation of the restriction enzyme. To this, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme NdeI to confirm the inserted restriction enzyme site.

The cloning vector comprising the PgapA sequence and the rrnBT1T2 terminator sequence was named pCRB209.

(3) Cloning of Aniline-Producing Genes

Cloning of Aniline-Producing Gene Derived from *Bacillus subtilis*

A DNA fragment comprising the bsdBCD (hereinafter indicated as dec/BS) gene which encodes aminobenzoate decarboxylase derived from *Bacillus subtilis* was amplified by the PCR method as described below.

In the PCR, the following set of primers was synthesized based on SEQ ID NO: 16 (the dec/BS gene of *Bacillus subtilis*) with the use of "394 DNA/RNA Synthesizer" made by Applied Biosystems for cloning of the dec/BS gene, and was used.

Primers for Dec/BS Gene Amplification

```
(a-6);
                                      (SEQ ID NO: 17)
5'-CTCT CATATG AAAGCAGAATTCAAGCGTAAAG-3'

(b-6);
                                      (SEQ ID NO: 18)
5'-CTCT CATATG GATCAAGCCTTTCGTTCCG-3'
```

Primers (a-6) and (b-6) each have an NdeI restriction enzyme site added thereto.

Cloning of Aniline-Producing Gene Derived from *Lactobacillus* Rhamnosus

A DNA fragment comprising the ubiDX (hereinafter indicated as dec/LR) gene which encodes aminobenzoate decarboxylase derived from *Lactobacillus rhamnosus* was amplified by the PCR method as described below.

In the PCR, the following set of primers was synthesized based on SEQ ID NO: 19 (the dec/LR gene of *Lactobacillus rhamnosus*) with the use of "394 DNA/RNA Synthesizer" made by Applied Biosystems for cloning of the dec/LR gene, and was used.

Primers for Dec/LR Gene Amplification

```
(a-7);
                                      (SEQ ID NO: 20)
5'-CTCT CATATG ACAGCATCACCTTGGG-3'

(b-7);
                                      (SEQ ID NO: 21)
5'-CTCT CATATG TCATCTTAACGACGCTCCATTC-3'
```

Primers (a-7) and (b-7) each have an NdeI restriction enzyme site added thereto.

Cloning of Aniline-Producing Gene Derived from *Lactobacillus brevis*

A DNA fragment comprising the LVIS_1987-LVIS_1986 (hereinafter indicated as dec/LB) gene which encodes aminobenzoate decarboxylase derived from *Lactobacillus brevis* was amplified by the PCR method as described below.

In the PCR, the following set of primers was synthesized based on SEQ ID NO: 22 (the dec/LB gene of *Lactobacillus brevis*) with the use of "394 DNA/RNA Synthesizer" made by Applied Biosystems for cloning of the dec/LB gene, and was used.

Primers for Dec/LB Gene Amplification

```
(a-8);
                                      (SEQ ID NO: 23)
5'-CTCT CATATG GTAAATGATCCTTATGATTTACGAAAAG-3'

(b-8);
                                      (SEQ ID NO: 24)
5'-CTCT CATATG CTAATCTCCCTCCCAACG-3'
```

Primers (a-8) and (b-8) each have an NdeI restriction enzyme site added thereto.

Cloning of Aniline-Producing Gene Derived from *Pseudomonas putida*

A DNA fragment comprising the ubiD (hereinafter indicated as dec/PP) gene which encodes aminobenzoate decarboxylase derived from *Pseudomonas putida* was amplified by the PCR method as described below.

In the PCR, the following set of primers was synthesized based on SEQ ID NO: 25 (the dec/PP gene of *Pseudomonas putida*) with the use of "394 DNA/RNA Synthesizer" made by Applied Biosystems for cloning of the dec/PP gene, and was used.

Primers for Dec/PP Gene Amplification

```
(a-9);
                                      (SEQ ID NO: 26)
5'-CTCT CATATG AACGGGCCGGAAC-3'

(b-9);
                                      (SEQ ID NO: 27)
5'-CTCT CATATG TCAATCATCCACCCCGAAG-3'
```

Primers (a-9) and (b-9) each have an NdeI restriction enzyme site added thereto.

Cloning of Aniline-Producing Gene Derived from *Escherichia coli*

A DNA fragment comprising the purEK (hereinafter indicated as dec/EC) gene which encodes aminobenzoate decarboxylase derived from *Escherichia coli* was amplified by the PCR method as described below.

In the PCR, the following set of primers was synthesized based on SEQ ID NO: 28 (the dec/EC gene of *Escherichia coli*) with the use of "394 DNA/RNA Synthesizer" made by Applied Biosystems for cloning of the dec/EC gene, and was used.

Primers for Dec/EC Gene Amplification

```
(a-10);
                                      (SEQ ID NO: 29)
5'-CTCT CATATG TCTTCCCGCAATAATCCG-3'

(b-10);
                                      (SEQ ID NO: 30)
5'-CTCT CATATG TTAACCGAACTTACTCTGCGC-3'
```

Primers (a-10) and (b-10) each have an NdeI restriction enzyme site added thereto.

Cloning of Aniline-Producing Gene Derived from *Saccharomyces cerevisiae*

A DNA fragment comprising the ADE2 (hereinafter indicated as dec/SC) gene which encodes aminobenzoate decarboxylase derived from *Saccharomyces cervisiae* was amplified by the PCR method as described below.

In the PCR, the following set of primers was synthesized based on SEQ ID NO: 31 (the dec/SC gene of *Saccharomyces cervisiae*) with use of "394 DNA/RNA Synthesizer" made by Applied Biosystems for cloning of the dec/SC gene, and was used.
Primers for Dec/SC Gene Amplification

```
(a-11);
                                       (SEQ ID NO: 32)
5'-CTCT CCATGG ATTCTAGAACAGTTGGTATATTAG-3'

(b-11);
                                       (SEQ ID NO: 33)
5'-CTCT CCATGG TTACTTGTTTTCTAGATAAGCTTCGTAAC-3'
```

Primers (a-11) and (b-11) each have an NcoI restriction enzyme site added thereto.
Cloning of Aniline-Producing Gene Derived from *Enterobacter cloacae*

A DNA fragment comprising the ECL_04083-ECL_04082-ECL_04081 (hereinafter indicated as dec/ECL) gene which encodes aminobenzoate decarboxylase derived from *Enterobacter cloacae* was amplified by the PCR method as described below.

In the PCR, the following set of primers was synthesized based on SEQ ID NO: 34 (the dec/ECL gene of *Enterobacter cloacae*) with the use of "394 DNA/RNA Synthesizer" made by Applied Biosystems for cloning of the dec/ECL gene, and was used.
Primers for Dec/ECL Gene Amplification

```
(a-12);
                                       (SEQ ID NO: 35)
5'-CTCT CATATG AGATTGATCGTGGGAATGAC-3'

(b-12);
                                       (SEQ ID NO: 36)
5'-CTCT CATATG TTACAGCAATGGCGGAATGG-3'
```

Primers (a-12) and (b-12) each have an NdeI restriction enzyme site added thereto.

As the template DNA for *Bacillus subtilis*, the chromosomal DNA extracted from *Bacillus subtilis* NBRC14144 obtained from NITE Biological Resource Center (NBRC) was used.

For *Lactobacillus rhamnosus*, the chromosomal DNA extracted from *Lactobacillus rhamnosus* NBRC3425 obtained from NITE Biological Resource Center (NBRC) was used.

For *Lactobacillus brevis*, the chromosomal DNA extracted from *Lactobacillus brevis* ATCC367 obtained from American Type Culture Collection (ATCC) was used.

For *Pseudomonas putida*, the chromosomal DNA extracted from *Pseudomonas putida* ATCC47054 obtained from American Type Culture Collection (ATCC) was used.

For *Escherichia coli*, the chromosomal DNA extracted from *Escherichia coli* K-12 MG1655 was used.

For *Saccharomyces cervisiae*, the chromosomal DNA extracted from *Saccharomyces cervisiae* NBRC10217 obtained from NITE Biological Resource Center (NBRC) was used.

For *Enterobacter cloacae*, the chromosomal DNA extracted from *Enterobacter cloacae* NBRC13535 obtained from NITE Biological Resource Center (NBRC) was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II ($Mg^{2+}$ free) | 5 µL |
| 25 mM $MgCl_2$ | 5 µL |
| dNTP Mixture (2.5 mM each) | 8 µL |
| Template DNA | 5 µL (DNA content: 1 µg or less) |
| The above 2 primers*) | 0.5 µL each (final conc.: 1 µM) |
| Sterile distilled water | 25.5 µL |

The above ingredients were mixed, and 50 µL of the reaction mixture was subjected to PCR.

*) For amplification of the dec/BS gene of *Bacillus subtilis*, a combination of primers (a-6) and (b-6);
for amplification of the dec/LR gene of *Lactobacillus rhamnosus*, a combination of primers (a-7) and (b-7);
for amplification of the dec/LB gene of *Lactobacillus brevis*, a combination of primers (a-8) and (b-8);
for amplification of the dec/PP gene of *Pseudomonas putida*, a combination of primers (a-9) and (b-9);
for amplification of the dec/EC gene of *Escherichia coli*, a combination of primers (a-10) and (b-10);
for amplification of the dec/SC gene of *Saccharomyces cervisiae*, a combination of primers (a-11) and (b-11); and
for amplification of the dec/ECL gene of *Enterobacter cloacae*, a combination of primers (a-12) and (b-12) were used.

PCR Cycle:
Denaturation step: 94° C., 60 seconds
Annealing step: 52° C., 60 seconds
Extension step: 72° C.

| | |
|---|---|
| *Bacillus subtilis* dec/BS gene | 137 seconds |
| *Lactobacillus rhamnosus* dec/LR gene | 123 seconds |
| *Lactobacillus brevis* dec/LB gene | 123 seconds |
| *Pseudomonas putida* dec/PP gene | 45 seconds |
| *Escherichia coli* dec/EC gene | 94 seconds |
| *Saccharomyces cervisiae* dec/SC gene | 103 seconds |
| *Enterobacter cloacae* dec/ECL gene | 135 seconds |

A cycle consisting of the above 3 steps was repeated 30 times.

With the use of 10 µL of the reaction mixture produced above, 0.8% agarose gel electrophoresis was performed. As a result, detected were an about 2.3-kb DNA fragment in the case of the *Bacillus subtilis* dec/BS gene, an about 2.1-kb DNA fragment in the case of the *Lactobacillus rhamnosus* dec/LR gene, an about 2.0-kb DNA fragment in the case of the *Lactobacillus brevis* dec/LB gene, an about 0.6-kb DNA fragment in the case of the *Pseudomonas putida* dec/PP gene, an about 1.6-kb DNA fragment in the case of the *Escherichia coli* dec/EC gene, an about 1.7-kb DNA fragment in the case of the *Saccharomyces* cervisiae dec/SC gene, and an about 2.3-kb DNA fragment in the case of the *Enterobacter cloacae* dec/ECL gene.

(4) Construction of Aniline-Producing Gene Expression Plasmids

Cloning of Aniline-Producing Gene to pCRB207

10 µL of the about 1.7-kb DNA fragment comprising the dec/SC gene derived from *Saccharomyces cerevisiae* amplified by the PCR in the above (3) and 2 µL of the cloning vector pCRB207 comprising a promoter PgapA were each cut with the use of restriction enzyme NcoI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid E.

With the use of the Ligation Liquid E, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment. As a result, in addition to an about 5.1-kb DNA fragment of the plasmid pCRB207, an about 1.7-kb inserted fragment of the dec/SC gene derived from *Saccharomyces cerevisiae* (Ligation Liquid E) was confirmed.

The plasmid comprising the dec/SC gene derived from *Saccharomyces cerevisiae* was named pCRB207-dec/SC (FIG. 1).

Cloning of Aniline-Producing Genes to pCRB209

10 µL of the about 2.3-kb DNA fragment comprising the dec/BS gene derived from *Bacillus subtilis*, the about 2.1-kb DNA fragment comprising the dec/LR gene derived from *Lactobacillus rhamnosus*, the about 2.0-kb DNA fragment comprising the dec/LB gene derived from *Lactobacillus brevis*, the about 0.6-kb DNA fragment comprising the dec/PP gene derived from *Pseudomonas putida*, the about 1.6-kb DNA fragment comprising the dec/EC gene derived from *Escherichia coli*, or the about 2.3-kb DNA fragment comprising the dec/ECL gene derived from *Enterobacter cloacae* amplified by the PCR in the above (3) and 2 µL of the cloning vector pCRB209 comprising a promoter PgapA were each cut with the use of restriction enzyme NdeI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. The resulting liquid was named Ligation Liquid F, G, H, I, J, or K.

With the use of each of the obtained 6 kinds of Ligation Liquids F, G, H, I, J, and K, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of restriction enzyme to confirm the inserted fragment. As a result, in addition to an about 5.1-kb DNA fragment of the plasmid pCRB209, confirmed were an about 2.3-kb inserted fragment in the case of the dec/BS gene derived from *Bacillus subtilis* (Ligation Liquid F), an about 2.1-kb inserted fragment in the case of the dec/LR derived from *Lactobacillus rhamnosus* (Ligation Liquid G), an about 2.0-kb inserted fragment in the case of the dec/LB gene derived from *Lactobacillus brevis* (Ligation Liquid H), an about 0.6-kb inserted fragment in the case of the dec/PP gene derived from *Pseudomonas putida* (Ligation Liquid I), an about 1.6-kb inserted fragment in the case of the dec/EC gene derived from *Escherichia coli* (Ligation Liquid J), and an about 2.3-kb inserted fragment in the case of the dec/ECL gene derived from *Enterobacter cloacae* (Ligation Liquid K).

The plasmid comprising the dec/BS gene derived from *Bacillus subtilis* was named pCRB209-dec/BS, the plasmid comprising the dec/LR gene derived from *Lactobacillus rhamnosus* was named pCRB209-dec/LR, the plasmid comprising the dec/LB gene derived from *Lactobacillus brevis* was named pCRB209-dec/LB, the plasmid comprising the dec/PP gene derived from *Pseudomonas putida* was named pCRB209-dec/PP, the plasmid comprising the dec/EC gene derived from *Escherichia coli* was named pCRB209-dec/EC, and the plasmid comprising the dec/ECL gene derived from *Enterobacter cloacae* was named pCRB209-dec/ECL (FIG. 1).

(5) Construction of Transgenic Strains for Aniline-Producing Gene

With the use of the above-described 7 kinds of plasmids pCRB209-dec/BS, pCRB209-dec/LR, pCRB209-dec/LB, pCRB209-dec/PP, pCRB209-dec/EC, pCRB207-dec/SC, and pCRB209-dec/ECL, transformation of *Corynebacterium glutamicum* R was performed by electroporation (Agric. Biol. Chem., Vol. 54, 443-447 (1990) and Res. Microbiol., Vol. 144, 181-185 (1993)), and each strain was applied to A agar medium containing 50 µg/mL of kanamycin.

A growing strain on the culture medium was subjected to liquid culture in the usual manner. Plasmid DNA was extracted from the culture and cut with the use of restriction enzyme to confirm the inserted plasmid. As a result, introduction of the above-constructed plasmids pCRB209-dec/BS, pCRB209-dec/LR, pCRB209-dec/LB, pCRB209-dec/PP, pCRB209-dec/EC, pCRB207-dec/SC, and pCRB209-dec/ECL was confirmed.

The strain to which the plasmid pCRB209-dec/BS had been introduced was named *Corynebacterium glutamicum* ANI-1, the strain to which the plasmid pCRB209-dec/LR had been introduced was named *Corynebacterium glutamicum* ANI-2, the strain to which the plasmid pCRB209-dec/LB had been introduced was named *Corynebacterium glutamicum* ANI-3, the strain to which the plasmid pCRB209-dec/PP had been introduced was named *Corynebacterium glutamicum* ANI-4, the strain to which the plasmid pCRB209-dec/EC had been introduced was named *Corynebacterium glutamicum* ANI-5, the strain to which the plasmid pCRB207-dec/SC had been introduced was named *Corynebacterium glutamicum* ANI-6, and the strain to which the plasmid pCRB209-dec/ECL had been introduced was named *Corynebacterium glutamicum* ANI-7.

*Corynebacterium glutamicum* ANI-1 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-1001 on Nov. 16, 2010.

Example 2

Experiment of Aniline Production from Anthranilic Acid Using *Corynebacterium glutamicum* Aniline-Producing Gene Transgenic Strains Each of the *Corynebacterium glutamicum* ANI-1 to ANI-7 strains constructed in Example 1 was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 µg/mL of kanamycin, and left stand in the dark at 33° C. for 20 hours.

An inoculation loop of each of the *Corynebacterium glutamicum* ANI-1 to ANI-7 strains grown on a plate as above was inoculated into a test tube containing 10 mL of A liquid medium containing 50 µg/mL of kanamycin, and aerobically cultured with shaking at 33° C. for 20 hours. The bacterial cells of each strain cultured and grown as above were collected by centrifugation (15,000×g at 4° C. for 10 minutes). The obtained bacterial cells were washed twice with 10 mL of BT liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution) and then suspended in the BT liquid medium in such a way that the bacterial cell concentration would be $OD_{610}$=10. To a 15-mL centrifuge tube, the cell suspension was transferred, anthranilic acid as a substrate was added so as to be 25 mM in concentration, and the reaction was allowed to proceed under reducing conditions (the ORP of the reaction mixture: −450 mV) in a water bath kept at 33° C. with stirring for 6 hours. A sample of the reaction mixture was centrifuged (15,000×g at 4° C. for 10 minutes), and the obtained supernatant was used for quantitative determination of aniline by GC/MS.

As a result, in the reaction under reducing conditions, the *Corynebacterium glutamicum* ANI-1 to ANI-7 strains had produced aniline as shown in Table 1 below.

TABLE 1

Experiment of aniline production of *Corynebacterium glutamicum* ANI-1 to ANI-7 strains with use of anthranilic acid as a substrate

| Strain | Host strain | Origin of aminobenzoate decarboxylase gene | Amount of aniline production (mM) |
|---|---|---|---|
| ANI-1 | *Corynebacterium* | *Bacillus subtilis* | 0.75 |
| ANI-2 | *glutamicum* | *Lactobacillus rhamnosus* | 0.7 |
| ANI-3 | (Wild strain) | *Lactobacillus brevis* | 0.6 |
| ANI-4 | | *Pseudomonas putida* | 0.6 |
| ANI-5 | | *Escherichia coli* | 0.5 |
| ANI-6 | | *Saccharomyces cerevisiae* | 0.5 |
| ANI-7 | | *Enterobacter cloacae* | 0.5 |

Without the addition of kanamycin to the culture medium, the same experiment as above was conducted using *Corynebacterium glutamicum* wild strain. In this case, aniline production was not observed.

Example 3

Experiment of Aniline Production from 4-Aminobenzoate Using *Corynebacterium glutamicum* Aniline-Producing Gene Transgenic Strains Each of the *Corynebacterium glutamicum* ANI-1 to ANI-7 strains constructed in Example 1 was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 µg/mL of kanamycin, and left stand in the dark at 33° C. for 20 hours.

An inoculation loop of each of the *Corynebacterium glutamicum* ANI-1 to ANI-7 strains grown on a plate as above was inoculated into a test tube containing 10 mL of A liquid medium containing 50 µg/mL of kanamycin, and aerobically cultured with shaking at 33° C. for 20 hours. The bacterial cells of each strain cultured and grown as above were collected by centrifugation (15,000×g at 4° C. for 10 minutes). The obtained bacterial cells were washed twice with 10 mL of BT liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution) and then suspended in BT liquid medium in such a way that the bacterial cell concentration would be $OD_{610}$=10. To a 15-mL centrifuge tube, the cell suspension was transferred, 4-aminobenzoate as a substrate was added so as to be 5 mM in concentration, and the reaction was allowed to proceed under reducing conditions (the ORP of the reaction mixture: −450 mV) in a water bath kept at 33° C. with stirring for 6 hours. A sample of the reaction mixture was centrifuged (15,000×g at 4° C. for 10 minutes), and the obtained supernatant was used for quantitative determination of aniline by GC/MS.

As a result, in the reaction under reducing conditions, the *Corynebacterium glutamicum* ANI-1 to ANI-7 strains had produced aniline as shown in Table 2 below.

TABLE 2

Experiment of aniline production of *Corynebacterium glutamicum* ANI-1 to ANI-7 strains with use of 4-aminobenzoate as a substrate

| Strain | Host strain | Origin of aminobenzoate decarboxylase gene | Amount of aniline production (mM) |
|---|---|---|---|
| ANI-1 | *Corynebacterium* | *Bacillus subtilis* | 0.7 |
| ANI-2 | *glutamicum* | *Lactobacillus rhamnosus* | 0.65 |
| ANI-3 | (Wild strain) | *Lactobacillus brevis* | 0.6 |
| ANI-4 | | *Pseudomonas putida* | 0.6 |
| ANI-5 | | *Escherichia coli* | 0.5 |
| ANI-6 | | *Saccharomyces cerevisiae* | 0.5 |
| ANI-7 | | *Enterobacter cloacae* | 1.25 |

Without the addition of kanamycin to the culture medium, the same experiment as above was conducted using *Corynebacterium glutamicum* wild strain. In this case, aniline production was not observed.

INDUSTRIAL APPLICABILITY

According to the process of the present invention, aniline can be produced from aminobenzoic acid with a practical efficiency using microorganisms.

The invention claimed is:

1. A process for producing aniline, comprising:
   A) contacting an aniline-producing coryneform bacterium with a reaction mixture comprising aminobenzoic acid, an ester thereof, and/or a salt thereof to produce aniline, and
   B) recovering said aniline from said reaction mixture, wherein said aniline-producing coryneform bacterium is transformed with a polynucleotide encoding an enzyme having aminobenzoate decarboxylase activity, wherein said polynucleotide comprises a nucleotide sequence selected from the group consisting of:
      (a) the nucleotide sequence of SEQ ID NO: 16, SEQ ID NO: 19, SEQ ID NO; 22, SEQ ID NO: 25, SEQ ID NO: 28, SEQ ID NO: 31 or SEQ ID NO: 34; and
      (b) a nucleotide sequence that has at least 95% nucleotide sequence identity with the nucleotide sequence of SEQ ID NO: 16, 19, 22, 25, 28, or 31, wherein said nucleotide sequence encodes a polypeptide having aminobenzoate decarboxylase activity.

2. The process of claim 1, wherein said aniline-producing coryneform bacterium is Corynebacterium glutamicum.

3. The process of claim 1, wherein said aniline-producing coryneform bacterium is selected from the group consisting of Coryneform glutamicum R (FERMI BP-18976), ATCC13032, and ATCC13869.

4. The process of claim 1, wherein step A) is conducted under reducing conditions.

5. The process of claim 4, wherein said aniline-producing coryneform bacterium does not grow in step A).

6. The process of claim 4, wherein an oxidation-reduction potential of said reaction mixture under reducing conditions is −200 mV to −500 mV.

* * * * *

UNITED STATES PATENT AND TRADEMARK OFFICE
CERTIFICATE OF CORRECTION

PATENT NO.      : 9,453,248 B2                    Page 1 of 1
APPLICATION NO. : 14/983178
DATED           : September 27, 2016
INVENTOR(S)     : Hideaki Yukawa et al.

It is certified that error appears in the above-identified patent and that said Letters Patent is hereby corrected as shown below:

In the Claims

In Column 54, Line 54, in Claim 3 reads:
Coryneform glutamicum R (FERMI BP-18976)

Should read:
Corynebacterium glutamicum R (FERM BP-18976)

Signed and Sealed this
Fourteenth Day of March, 2017

Michelle K. Lee
*Director of the United States Patent and Trademark Office*

SEQUENCE LISTING

<160> NUMBER OF SEQ ID NOS: 36

<210> SEQ ID NO 1
<211> LENGTH: 1195
<212> TYPE: DNA
<213> ORGANISM: Artificial sequence
<220> FEATURE:
<223> OTHER INFORMATION: pCASE1-ori

<400> SEQUENCE: 1

| | | | | | |
|---|---|---|---|---|---|
| atgaaaaccg | accgtgcacg | ctcgtgtgag | aaagtcagct | acatgagacc | aactacccgc | 60 |
| cctgagggac | gctttgagca | gctgtggctg | ccgctgtggc | cattggcaag | cgatgacctc | 120 |
| cgtgagggca | tttaccgcac | ctcacggaag | aacgcgctgg | ataagcgcta | cgtcgaagcc | 180 |
| aatcccgacg | cgctctctaa | cctcctggtc | gttgacatcg | accaggagga | cgcgcttttg | 240 |
| cgctctttgt | gggacaggga | ggactggaga | cctaacgcgg | tggttgaaaa | ccccttaaac | 300 |
| gggcacgcac | acgctgtctg | ggcgctcgcg | gagccattta | cccgcaccga | atacgccaaa | 360 |
| cgcaagcctt | tggcctatgc | cgcggctgtc | accgaaggcc | tacggcgctc | tgtcgatggc | 420 |
| gatagcggat | actccgggct | gatcaccaaa | aaccccgagc | acactgcatg | ggatagtcac | 480 |
| tggatcaccg | ataagctgta | tacgctcgat | gagctgcgct | tttggctcga | agaaaccggc | 540 |
| tttatgccgc | ctgcgtcctg | gaggaaaacg | cggcggttct | cgccagttgg | tctaggtcgt | 600 |
| aattgcgcac | tctttgaaag | cgcacgtacg | tgggcatatc | gggaggtcag | aaagcatttt | 660 |
| ggagacgctg | acggcctagg | ccgcgcaatc | caaaccaccg | cgcaagcact | taaccaagag | 720 |
| ctgtttgatg | aaccactacc | tgtggccgaa | gttgactgta | ttgccaggtc | aatccataaa | 780 |
| tggatcatca | ccaagtcacg | catgtggaca | acggcgccg | ccgtctacga | cgccacattc | 840 |
| accgcaatgc | aatccgcacg | cgggaagaaa | ggctggcaac | gaagcgctga | ggtgcgtcgt | 900 |
| gaggctggac | atactctttg | gaggaacatt | ggctaaggtt | tatgcacgtt | atccacgcaa | 960 |
| cggaaaaaca | gcccgcgagc | tggcagaacg | tgccggtatg | tcggtgagaa | cagctcaacg | 1020 |
| atggacttcc | gaaccgcgtg | aagtgttcat | taaacgtgcc | aacgagaagc | gtgctcgcgt | 1080 |
| ccaggagctg | cgcgccaaag | gtctgtccat | gcgcgctatc | gcggcagaga | ttggttgctc | 1140 |
| ggtgggcacg | gttcaccgct | acgtcaaaga | agttgaagag | aagaaaaccg | cgtaa | 1195 |

<210> SEQ ID NO 2
<211> LENGTH: 2675
<212> TYPE: DNA
<213> ORGANISM: Artificial sequence
<220> FEATURE:
<223> OTHER INFORMATION: pHSG298

<400> SEQUENCE: 2

| | | | | | |
|---|---|---|---|---|---|
| gaggtctgcc | tcgtgaagaa | ggtgttgctg | actcatacca | ggcctgaatc | gccccatcat | 60 |
| ccagccagaa | agtgagggag | ccacggttga | tgagagcttt | gttgtaggtg | gaccagttgg | 120 |
| tgattttgaa | cttttgcttt | gccacggaac | ggtctgcgtt | gtcgggaaga | tgcgtgatct | 180 |
| gatccttcaa | ctcagcaaaa | gttcgattta | ttcaacaaag | ccacgttgtg | tctcaaaatc | 240 |
| tctgatgtta | cattgcacaa | gataaaaata | tatcatcatg | aacaataaaa | ctgtctgctt | 300 |
| acataaacag | taatacaagg | ggtgttatga | gccatattca | acgggaaacg | tcttgctcga | 360 |
| agccgcgatt | aaattccaac | atggatgctg | atttatatgg | gtataaatgg | gctcgcgata | 420 |
| atgtcgggca | atcaggtgcg | acaatctatc | gattgtatgg | gaagcccgat | gcgccagagt | 480 |
| tgtttctgaa | acatggcaaa | ggtagcgttg | ccaatgatgt | tacagatgag | atggtcagac | 540 |

```
taaactggct gacggaattt atgcctcttc cgaccatcaa gcattttatc cgtactcctg      600
atgatgcatg gttactcacc actgcgatcc ccgggaaaac agcattccag gtattagaag      660
aatatcctga ttcaggtgaa aatattgttg atgcgctggc agtgttcctg cgccggttgc      720
attcgattcc tgtttgtaat tgtccttttg acagcgatcg cgtatttcgt ctcgctcagg      780
cgcaatcacg aatgaataac ggtttggttg atgcgagtga ttttgatgac gagcgtaatg      840
gctggcctgt tgaacaagtc tggaaagaaa tgcataagct tttgccattc tcaccggatt      900
cagtcgtcac tcatggtgat ttctcacttg ataaccttat ttttgacgag gggaaattaa      960
taggttgtat tgatgttgga cgagtcggaa tcgcagaccg ataccaggat cttgccatcc     1020
tatggaactg cctcggtgag ttttctcctt cattacagaa acggcttttt caaaaatatg     1080
gtattgataa tcctgatatg aataaattgc agtttcattt tgatgctcga tgagttttct     1140
aatcagaatt ggttaattgg ttgtaacact ggcagagcat tacgctgact tgacgggacg     1200
gcggctttgt tgaataaatc gcattcgcca ttcaggctgc gcaactgttg ggaagggcga     1260
tcggtgcggg cctcttcgct attacgccag ctggcgaaag ggggatgtgc tgcaaggcga     1320
ttaagttggg taacgccagg gttttcccag tcacgacgtt gtaaaacgac ggccagtgcc     1380
aagcttgcat gcctgcaggt cgactctaga ggatccccgg gtaccgagct cgaattcgta     1440
atcatgtcat agctgtttcc tgtgtgaaat tgttatccgc tcacaattcc acacaacata     1500
cgagccggaa gcataaagtg taaagcctgg ggtgcctaat gagtgagcta actcacatta     1560
attgcgttgc gctcactgcc cgctttccag tcgggaaacc tgtcgtgcca gctgcattaa     1620
tgaatcggcc aacgcgcggg gagaggcggt ttgcgtattg gcgaactttt gctgagttga     1680
aggatcagat cacgcatctt cccgacaacg cagaccgttc cgtggcaaag caaaagttca     1740
aaatcagtaa ccgtcagtgc cgataagttc aaagttaaac ctggtgttga taccaacatt     1800
gaaacgctga tcgaaaacgc gctgaaaaac gctgctgaat gtgcgagctt cttccgcttc     1860
ctcgctcact gactcgctgc gctcggtcgt tcggctgcgg cgagcggtat cagctcactc     1920
aaaggcggta atacggttat ccacagaatc aggggataac gcaggaaaga acatgtgagc     1980
aaaaggccag caaaaggcca ggaaccgtaa aaaggccgcg ttgctggcgt ttttccatag     2040
gctccgcccc cctgacgagc atcacaaaaa tcgacgctca agtcagaggt ggcgaaaccc     2100
gacaggacta taaagatacc aggcgtttcc ccctggaagc tccctcgtgc gctctcctgt     2160
tccgaccctg ccgcttaccg gatacctgtc cgcctttctc ccttcgggaa gcgtggcgct     2220
ttctcaatgc tcacgctgta ggtatctcag ttcggtgtag gtcgttcgct ccaagctggg     2280
ctgtgtgcac gaaccccccg ttcagcccga ccgctgcgcc ttatccggta actatcgtct     2340
tgagtccaac ccggtaagac acgacttatc gccactggca gcagccactg gtaacaggat     2400
tagcagagcg aggtatgtag gcggtgctac agagttcttg aagtggtggc ctaactacgg     2460
ctacactaga aggacagtat ttggtatctg cgctctgctg aagccagtta ccttcggaaa     2520
aagagttggt agctcttgat ccggcaaaca aaccaccgct ggtagcggtg gttttttgt      2580 ttgcaagcag cagattacgc gcagaaaaaa aggatctcaa gaagatcctt tgatcttttc     2640
tacggggtct gacgctcagt ggaacgatcc gtcga                                2675
```

<210> SEQ ID NO 3
<211> LENGTH: 25
<212> TYPE: DNA
<213> ORGANISM: Artificial sequence
<220> FEATURE:

```
<223> OTHER INFORMATION: PCR primer

<400> SEQUENCE: 3
atagatctag aacgtccgta ggagc                                          25

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
atagatctga cttggttacg atggac                                         26

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
atagatctag gtttcccgac tggaaag                                        27

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
atagatctcg tgccagctgc attaatga                                       28

<210> SEQ ID NO 7
<211> LENGTH: 551
<212> TYPE: DNA
<213> ORGANISM: Corynebacterium glutamicum

<400> SEQUENCE: 7
ccgaagatct gaagattcct gatacaaatt ctgttgtgac ggaagatttg ttggaagaaa    60
tctagtcgct cgtctcataa aaacgaccga gcctattggg attaccattg aagccagtgt   120
gagttgcatc acactggctt caaatctgag actttacttt gtggattcac ggggtgtag    180 tgcaattcat aattagcccc attcggggga gcagatcgcg gcgcgaacga tttcaggttc   240
gttccctgca aaaactattt agcgcaagtg ttggaaatgc ccccgtctgg ggtcaatgtc   300 tattttgaa tgtgtttgta tgattttgaa tccgctgcaa aatctttgtt tccccgctaa    360
agttggggac aggttgacac ggagttgact cgacgaatta tccaatgtga gtaggtttgg   420
tgcgtgagtt ggaaaatttc gccatactcg cccttgggtt ctgtcagctc aagaattctt   480
gagtgaccga tgctctgatt gacctaactg cttgacacat tgcatttcct acaatcttta   540
gaggagacac a                                                        551

<210> SEQ ID NO 8
<211> LENGTH: 425
<212> TYPE: DNA
<213> ORGANISM: Artificial sequence
<220> FEATURE:
<223> OTHER INFORMATION: rrnBT1T2 terminator

<400> SEQUENCE: 8
```

-continued

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gttttatctg ttgtttgtcg gtgaacgctc tcctgagtag acaaatccgc cgggagcgg      300 atttgaacgt tgcgaagcaa cggcccggag ggtggcgggc aggacgcccg ccataaactg     360
ccaggcatca aattaagcag aaggccatcc tgacggatgg ccttttttgcg tttctacaaa    420 ctctt                                                                 425
```

<210> SEQ ID NO 9
<211> LENGTH: 31
<212> TYPE: DNA
<213> ORGANISM: Artificial sequence
<220> FEATURE:
<223> OTHER INFORMATION: PCR primer

<400> SEQUENCE: 9

```
ctctgtcgac ccgaagatct gaagattcct g                                     31
```

<210> SEQ ID NO 10
<211> LENGTH: 46
<212> TYPE: DNA
<213> ORGANISM: Artificial sequence
<220> FEATURE:
<223> OTHER INFORMATION: PCR primer

<400> SEQUENCE: 10

```
ctctgtcgac ggatccccat ggtgtgtctc tctaaagat tgtagg                      46
```

<210> SEQ ID NO 11
<211> LENGTH: 36
<212> TYPE: DNA
<213> ORGANISM: Artificial sequence
<220> FEATURE:
<223> OTHER INFORMATION: PCR primer

<400> SEQUENCE: 11

```
ctctgcatgc ccatggctgt tttggcggat gagaga                                36
```

<210> SEQ ID NO 12
<211> LENGTH: 41
<212> TYPE: DNA
<213> ORGANISM: Artificial sequence
<220> FEATURE:
<223> OTHER INFORMATION: PCR primer

<400> SEQUENCE: 12

```
ctctgcatgc tcatgaaaga gtttgtagaa acgcaaaaag g                          41
```

<210> SEQ ID NO 13
<211> LENGTH: 5118
<212> TYPE: DNA
<213> ORGANISM: Artificial sequence
<220> FEATURE:
<223> OTHER INFORMATION: pCRB207

<400> SEQUENCE: 13

```
agatctaggt ttcccgactg gaaagcgggc agtgagcgca acgcaattaa tgtgagttag      60
ctcactcatt aggcacccca ggctttacac tttatgcttc cggctcgtat gttgtgtgga     120
```

```
attgtgagcg ataacaatt tcacacagga aacagctatg accatgatta cgaattcgag      180
ctcggtaccc ggggatcctc tagagtcgac ccgaagatct gaagattcct gatacaaatt      240
ctgttgtgac ggaagatttg ttggaagaaa tctagtcgct cgtctcataa aaacgaccga      300
gcctattggg attaccattg aagccagtgt gagttgcatc acactggctt caaatctgag      360
actttacttt gtggattcac gggggtgtag tgcaattcat aattagcccc attcgggggta     420 gcagatcgcg gcgcgaacga tttcaggttc gttccctgca aaactatttt agcgcaagtg      480
ttggaaatgc ccccgtctgg ggtcaatgtc tattttttgaa tgtgtttgta tgattttgaa     540
tccgctgcaa aatctttgtt tccccgctaa agttggggac aggttgacac ggagttgact      600
cgacgaatta tccaatgtga gtaggtttgg tgcgtgagtt ggaaaatttc gccatactcg      660
cccttgggtt ctgtcagctc aagaattctt gagtgaccga tgctctgatt gacctaactg      720
cttgacacat tgcatttcct acaatcttta gaggagacac accatggctg ttttggcgga      780
tgagagaaga ttttcagcct gatacagatt aaatcagaac gcagaagcgg tctgataaaa      840
cagaatttgc ctggcggcag tagcgcggtg gtcccacctg accccatgcc gaactcagaa      900
gtgaaacgcc gtagcgccga tggtagtgtg gggtctcccc atgcgagagt agggaactgc      960
caggcatcaa ataaaacgaa aggctcagtc gaaagactgg gcctttcgtt ttatctgttg     1020
tttgtcggtg aacgctctcc tgagtaggac aaatccgccg ggagcggatt tgaacgttgc     1080
gaagcaacgg cccggagggt ggcgggcagg acgcccgcca taaactgcca ggcatcaaat     1140
taagcagaag gccatcctga cggatggcct ttttgcgttt ctacaaactc tttcatgggg     1200
atccgtcgac ctgcaggcat gcaagcttgg cactggccgt cgttttacaa cgtcgtgact     1260
gggaaaaccc tggcgttacc caacttaatc gccttgcagc acatccccct tcgccagct     1320 ggcgtaatag cgaagaggcc cgcaccgatc gcccttccca acagttgcgc agcctgaatg     1380
gcgaatgcga tttattcaac aaagccgccg tcccgtcaag tcagcgtaat gctctgccag     1440
tgttacaacc aattaaccaa ttctgattag aaaaactcat cgagcatcaa atgaaactgc     1500
aatttattca tatcaggatt atcaatacca tatttttgaa aaagccgttt ctgtaatgaa     1560
ggagaaaact caccgaggca gttccatagg atggcaagat cctggtatcg gtctgcgatt     1620
ccgactcgtc caacatcaat acaacctatt aatttcccct cgtcaaaaat aaggttatca     1680
agtgagaaat caccatgagt gacgactgaa tccggtgaga atggcaaaag cttatgcatt     1740
tctttccaga cttgttcaac aggccagcca ttacgctcgt catcaaaatc actcgcatca     1800
accaaaccgt tattcattcg tgattgcgcc tgagcgagac gaaatacgcg atcgctgtta     1860
aaaggacaat tacaaacagg aatcgaatgc aaccggcgca ggaacactgc cagcgcatca     1920
acaatatttt cacctgaatc aggatattct tctaatacct ggaatgctgt tttcccgggg     1980
atcgcagtgg tgagtaacca tgcatcatca ggagtacgga taaaatgctt gatggtcgga     2040
agaggcataa attccgtcag ccagtttagt ctgaccatct catctgtaac atcattggca     2100
acgctacctt tgccatgttt cagaaacaac tctggcgcat cgggcttccc atacaatcga     2160
tagattgtcg cacctgattg cccgacatta tcgcgagccc atttataccc atataaatca     2220
gcatccatgt tggaatttaa tcgcggcttc gagcaagacg tttcccgttg aatatggctc     2280
ataacacccc ttgtattact gtttatgtaa gcagacagtt ttattgttca tgatgatata     2340
tttttatctt gtgcaatgta acatcagaga ttttgagaca acgtggct ttgttgaata      2400 aatcgaactt ttgctgagtt gaaggatcag atcacgcatc ttcccgacaa cgcagaccgt     2460
tccgtggcaa agcaaaagtt caaaatcacc aactggtcca cctacaacaa agctctcatc     2520
```

```
aaccgtggct ccctcacttt ctggctggat gatgggcga ttcaggcctg gtatgagtca    2580
gcaacacctt cttcacgagg cagacctctc gacggagttc cactgagcgt cagacccgt    2640 agaaaagatc aaaggatctt cttgagatcc ttttttctg cgcgtaatct gctgcttgca    2700
aacaaaaaaa ccaccgctac cagcggtggt ttgtttgccg gatcaagagc taccaactct    2760
ttttccgaag gtaactggct tcagcagagc gcagatacca aatactgttc ttctagtgta    2820
gccgtagtta ggccaccact tcaagaactc tgtagcaccg cctacatacc tcgctctgct    2880
aatcctgtta ccagtggctg ctgccagtgg cgataagtcg tgtcttaccg ggttggactc    2940
aagacgatag ttaccggata aggcgcagcg gtcgggctga acggggggtt cgtgcacaca    3000
gcccagcttg gagcgaacga cctacaccga actgagatac ctacagcgtg agctatgaga    3060
aagcgccacg cttcccgaag ggagaaaggc ggacaggtat ccggtaagcg gcagggtcgg    3120
aacaggagag cgcacgaggg agcttccagg gggaaacgcc tggtatcttt atagtcctgt    3180
cgggtttcgc cacctctgac ttgagcgtcg attttttgtga tgctcgtcag ggggggcggag   3240 cctatggaaa aacgccagca acgcggcctt tttacggttc ctggccttttt gctggccttt    3300 tgctcacatg ttctttcctg cgttatcccc tgattctgtg gataaccgta ttaccgcctt    3360
tgagtgagct gataccgctc gccgcagccg aacgaccgag cgcagcgagt cagtgagcga    3420
ggaagcggaa gaagctcgca cattcagcag cgttttttcag cgcgttttcg atcaacgttt    3480
caatgttggt atcaacacca ggtttaactt tgaacttatc ggcactgacg gttactgatt    3540
ttgaactttt gctttgccac ggaacggtct gcgttgtcgg gaagatgcgt gatctgatcc    3600
ttcaactcag caaaagttcg ccaatacgca aaccgcctct ccccgcgcgt tggccgattc    3660
attaatgcag ctggcacgag atctgacttg gttacgatgg actttgaaca cgccgagggt    3720
gactaaaccg ctggatttac gcggttttct tctcttcaac ttctttgacg tagcggtgaa    3780
ccgtgcccac cgagcaacca atctctgccg cgatagcgcg catggacaga cctttggcgc    3840
gcagctcctg gacgcgagca cgcttctcgt tggcacgttt aatgaacact tcacgcggtt    3900
cggaagtcca tcgttgagct gttctcaccg acataccggc acgttctgcc agctcgcggg    3960 ctgttttttcc gttgcgtgga taacgtgcat aaaccttagc caatgttcct ccaaagagta    4020
tgtccagcct cacgacgcac ctcagcgctt cgttgccagc ctttcttccc gcgtgcggat    4080
tgcattgcgg tgaatgtggc gtcgtagacg gcggcgccgt ctgtccacat gcgtgacttg    4140
gtgatgatcc atttatggat tgacctggca atacagtcaa cttcggccac aggtagtggt    4200
tcatcaaaca gctcttggtt aagtgcttgc gcggtggttt ggattgcgcg gcctaggccg    4260
tcagcgtctc caaaatgctt tctgacctcc cgatatgccc acgtacgtgc gctttcaaag    4320
agtgcgcaat tacgacctag accaactggc gagaaccgcc gcgttttcct ccaggacgca    4380
ggcggcataa agccggtttc ttcgagccaa aagcgcagct catcgagcgt atacagctta    4440
tcggtgatcc agtgactatc ccatgcagtg tgctcggggt ttttggtgat cagcccggag    4500
tatccgctat cgccatcgac agagcgccgt aggccttcgg tgacagccgc ggcataggcc    4560
aaaggcttgc gtttggcgta ttcggtgcgg gtaaatggct ccgcgagcgc ccagacagcg    4620
tgtgcgtgcc cgtttaaggg gttttcaacc accgcgttag gtctccagtc ctccctgtcc    4680
cacaaagagc gcaaaagcgc gtcctcctgg tcgatgtcaa cgaccaggag gttagagagc    4740 gcgtcggat tggcttcgac gtagcgctta ccagcgcgt tcttccgtga ggtgcggtaa    4800
atgccctcac ggaggtcatc gcttgccaat ggccacagcg gcagccacag ctgctcaaag    4860
```

```
cgtccctcag ggcgggtagt tggtctcatg tagctgactt tctcacacga gcgtgcacgg      4920
tcggttttca ttcataatac gacatttaac caagtcagat gtttcccggg tttccggggg      4980
ttcccctgaa gaaccttcc agtgcgagcg aagcgagctc ctttggccgg cgcccctcag       5040
gtagccctct aaggctccca gggctccgcc cctccctgag gttggctcaa gcctcctggt      5100
ggctcctacg gacgttct                                                    5118

<210> SEQ ID NO 14
<211> LENGTH: 29
<212> TYPE: DNA
<213> ORGANISM: Artificial sequence
<220> FEATURE:
<223> OTHER INFORMATION: PCR primer

<400> SEQUENCE: 14
ctctcatatg ctgttttggc ggatgagag                                          29

<210> SEQ ID NO 15
<211> LENGTH: 33
<212> TYPE: DNA
<213> ORGANISM: Artificial sequence
<220> FEATURE:
<223> OTHER INFORMATION: PCR primer

<400> SEQUENCE: 15
ctctcatatg gtgtctcctc taaagattgt agg                                     33

<210> SEQ ID NO 16
<211> LENGTH: 2285
<212> TYPE: DNA
<213> ORGANISM: Bacillus subtilis

<400> SEQUENCE: 16
atgaaagcag aattcaagcg taaaggaggg ggcaaagtga aactcgttgt cggaatgaca       60
ggggcaacag gggccatttt cggggtcagg ctgctgcagt ggctgaaggc cgccggagtg     120
gaaacccatc tcgttgtgtc tccttgggca aacgtcacga tcaaacacga aacaggctat    180
acgttacaag aagtagaaca actggccaca tacacttact cacataagga tcaggcggca    240
gccatttcaa gcgggtcgtt tgataccgat ggaatgattg ttgcgccgtg cagcatgaaa    300
tctctcgcaa gcattcgcac aggaatggcg ataatctgc tgacacgtgc ggcggatgtc     360
atgctcaagg agagaaaaaa actcgtcctc ttaacgagag agacgccttt gaaccaaatt    420
catctcgaaa atatgctagc gcttacgaaa atgggcacca tcattcttcc tccgatgccg    480
gcattttata atcggccgag aagcttagag gaaatggttg accatattgt ttttagaacg    540
ttggaccaat tcggcattcg gcttcctgaa gcgaagcgct ggaatgggat tgaaaaacaa    600
aaaggaggag cttgatcatg gcttatcaag atttcagaga atttctcgct gcccttgaaa    660
aagaaggaca gctgcttaca gtgaatgaag aggtaaagcc ggaaccggat ttaggggcct    720
ccgcacgggc agccagcaat cttggcgata aaagccctgc gctcttattt aacaacattt    780
acggctatca taacgcgcga attgcgatga atgtcatcgg ctcttggcca aaccatgcca    840
tgatgctggg catgccgaaa gacacaccgg taaagaaca gttttttgaa ttcgcaaagc     900
gttatgacca gtttccgatg ccggtcaaac gtgaggaaac agcgccattt catgaaaatg    960
aaatcacaga agatatcaat ttgttcgata tactgcctct tttcagaatt aaccagggtg   1020
atggaggcta ctatttagac aaagcatgtg tcatttcccg tgatcttgag gaccctgaca   1080
acttcggcaa acaaaatgtc ggcatttaca gaatgcaagt caaaggaaaa gaccgccttg   1140
```

-continued

```
gcattcagcc tgtcccgcag cacgatattg caatccatct gcgccaagct gaagaacgcg      1200
gcatcaacct tccggtcact attgcgctcg gctgtgagcc ggtcattaca acggcggcat      1260
cgactccgct tctctatgat caatcagaat cgaaatggc aggtgcgatt caaggcgaac       1320
catatcgcat cgtcaaatca aagctgtctg atcttgatgt tccgtggggc gctgaagtgg      1380
tgcttgaagg tgagattatt gccggagagc gcgaatatga agggccgttc ggtgaattca      1440
caggccatta ttccggcgga cgcagcatgc cgattatcaa aattaaacgc gtctatcaca      1500
gaaacaatcc gatctttgaa catttatact taggcatgcc ttggacagaa tgcgattaca      1560
tgatcggcat taacacatgc gtgccgcttt atcagcagtt aaaagaagcg tatccgaacg      1620
aaattgtggc agtgaacgcc atgtacacac acggtttaat cgcgattgtt ccacaaaaa      1680 cccgctatgg cggatttgcg aaagcggtcg gcatgcgcgc actcacaacg ccgcacggac      1740
tcggctactg caaaatggtc atagtcgttg atgaggatgt cgatccattc aaccttccgc      1800
aggtcatgtg ggcgctttcg accaaaatgc atccgaaaca tgatgcggtc atcattccgg      1860
acttatctgt cctgccgctt gatccgggat ccaatccatc aggaatcact cacaaaatga      1920
ttctcgacgc cactacaccg gttgcgccgg aaacaagagg ccattattca cagccgcttg      1980
attctccgct aacaacgaaa gaatgggaac aaaaactaat ggacttaatg aataaataag      2040
gaaaggatgt tcgaaatgca tacatgtcct cgatgcgact caaaaaaggg agaagtcatg      2100
agcaaatcgc ctgtagaagg cgcatgggaa gtttatcagt gccaaacatg cttttttaca      2160
tggagatcct gtgaaccgga aagcattaca aatcccgaaa aatacaatcc agcgtttaaa      2220
attgatccaa aggaaacaga aacagcaatt gaagttccgg cggtgccgga acgaaaggct      2280
tgatc                                                                 2285
```

<210> SEQ ID NO 17
<211> LENGTH: 32
<212> TYPE: DNA
<213> ORGANISM: Artificial sequence
<220> FEATURE:
<223> OTHER INFORMATION: PCR primer

<400> SEQUENCE: 17

```
ctctcatatg aaagcagaat tcaagcgtaa ag                                     32
```

<210> SEQ ID NO 18
<211> LENGTH: 29
<212> TYPE: DNA
<213> ORGANISM: Artificial sequence
<220> FEATURE:
<223> OTHER INFORMATION: PCR primer

<400> SEQUENCE: 18

```
ctctcatatg gatcaagcct ttcgttccg                                         29
```

<210> SEQ ID NO 19
<211> LENGTH: 2058
<212> TYPE: DNA
<213> ORGANISM: Lactobacillus rhamnosus

<400> SEQUENCE: 19

```
atgacagcat caccttggga cttaagaaaa gtattggatg aactaaaaca ggatccgcag        60
caatatcatg aaacagaggt gcaagtcgat cccgatgcag agcttgctgg cgtttatcgt       120
tacatcggtg ccggtgggac ggtcgaacgt ccgacacagg aaggtccggc aatgatgttt       180
```

```
aacaacgttg tcggcttccc aacgacaagg gttttgatcg gtttaatggc cagtcgcaag    240
cgggttggca agatgtttca ccaagactat cacacacttg gtcgattctt gaacaaagcg    300
gttttaaatc ctattcaacc cgttacagtc gaagaatcag cagcgcctgc gcatgaagtc    360
gttgccaagg ctagtgaccc ggactttgac attagaaaac tcgttgcagc accaaccaat    420
acgccacaag atgccggccc atacatcaca tgcggcgtag ttttgggttc caatatggcc    480
aaaacaatga ctgatgtgac gattcatcgc atggttttgg aagataagga tacgcttggt    540
atttatatca tgcccggtgg tcgccacatt ggtcattttg ctgaagaata tgaaaaagcc    600
aataagccga tgccggtgac catcaacatt ggcttggatc cggccattac cattggtgcc    660
acttttgaac cgcctaccac gccgcttggc tacgatgaac taggagttgc cggagccatt    720
cgccaagaac ccgtgcaact ggttcaggct gtgaccgtca atgaaaaagc cattgcgcgt    780
tcagaattta cactggaagg ctatatcatg cctaacacgc gtatccaaga agatatcaat    840
acccataccg gcaaagccat gccagagttt cccggctatg acggtgatgc caatccggct    900
ttgcaagtga ttaaagtgac ggctgtaacc catcggcgcg atcatcccat tatgcaaagt    960
gtcatcggac ctagtgaaga acatgtctcc atggccggca ttccaaccga agccagcatt   1020
ttacaacttg ttgatcgtgc catccccggc aaggtcaaga atgtgtacaa tcccccagct   1080
ggtggcggca aactcatgac catcatgcaa attcacaaag ataatccagc tgatgaaggg   1140
attcaacgtc aagctgcatt actcgctttt tcggcattca aagaactaaa aactgtttgg   1200
ctggtcgatg atgatgtcga tatttttgac atgaatgatg tcgtctggac aatgaacacg   1260
cgttttcaag gtgatcagga catcatggta ttacctggca tgcgcaacca tccgcttgat   1320
ccgtcagaac gaccgcaata tgatcccaag tctattcggg tacgcggaat gagttcgaag   1380
acggtcattg atggtaccgt accatttgat atgcgcgatc aattcaaacg agcagccttt   1440
aaaaaagttt ccgactggca aaaatatttg aaataggtga ttgaattgaa acgtattatc   1500
gtagggatta ccggggcatc cggaactatt tacgctgtta acctgctcca gcatttacat   1560
cgcctgcctg atgtcgaagt tcatttggtg atgagtgctt gggcaaagca aaacctgtca   1620
cttgagaccg acatgaaaca aagcgaactc gaagctttgg cggattatgt ttatcctgtt   1680
caaaaccaag gggcaaccat tgcaagcggc agttttttaa ccgatgcaat ggtcattgtt   1740
ccggcaagca tgaaaaccat tgcgggcatt gcgatgggct ttgatgataa tctcattgga   1800
cgagcagccg atgtcacgat taaagaacag cggcaattga ttattgtgcc gcgggaaaca   1860
ccgcttagtc caattcatct ggataaactc gctaaactag cccacattgg cgttcaaatc   1920
attccgccta ttccagcttt ctatcagcat ccccaaacca tccaggattt aattgagcat   1980
cacaccatga aactattaga cgccttgcat attaaaaccg aaaccgctag tcgctggaat   2040
ggagcgtcgt taagatga                                                2058
```

<210> SEQ ID NO 20
<211> LENGTH: 26
<212> TYPE: DNA
<213> ORGANISM: Artificial sequence
<220> FEATURE:
<223> OTHER INFORMATION: PCR primer

<400> SEQUENCE: 20
ctctcatatg acagcatcac cttggg                                          26

<210> SEQ ID NO 21
<211> LENGTH: 32

<212> TYPE: DNA
<213> ORGANISM: Artificial sequence
<220> FEATURE:
<223> OTHER INFORMATION: PCR primer

<400> SEQUENCE: 21

```
ctctcatatg tcatcttaac gacgctccat tc                                32
```

<210> SEQ ID NO 22
<211> LENGTH: 2045
<212> TYPE: DNA
<213> ORGANISM: Lactobacillus brevis

<400> SEQUENCE: 22

```
atggtaaatg atccttatga tttacgaaaa gtattggccg agctaaaaac ccatgccaac      60
cagtaccatg agacgaacgt agctgtgaat ccaaatgctg aattggctgg tgtttaccgc     120
tatattggtg ctggagggac ggtaaaacgg ccgacgcaag aaggtccagc aatgatgttt     180
aataacgttg aaggcttctc cgatacgaaa gtcctaatgg gattaatggc aaatcggcga     240
cgagtggggc tcatgttcca tcatgattac caaaccctgg aaaatttct aaatacagcg      300
gttgaaaaac caatccccccc agtgatggtt actgacgcac ctacccacga ggtggttcac     360
aaggccactg atccggactt tgatattcgt aaactcgttg cagcacctac gaatacaccg     420
gaggacgcgg gaccttacat tacagtgggt gtcgtgttgg gatctaatat ggccaagact     480
atgtcagatg tgacgattca ccgaatggtt ctagaagata aagacaagtt agggatttac     540
attatgcctg gcggtcggca tattggtgcc tttgctaaag aatacgaggc cgctaataaa     600
ccgatgccca tcacgattaa tattgggtta gatccggcca ttacgattgg gtgcaccttt     660
gagccaccaa ctacaccatt ggggtataac gagctggggg tggctggtgc gatccgacaa     720
gaagctgtgg gtctgaccaa agcgctaacc gttgatgaga atgctattgc ccgttctgaa     780
ttcacgttgg aagggtatat catgcccaac gaacggatgc aagaggatat caatacccag     840
acaggtaagg caatgcctga atttccgggt tacgacggtg atgctaatcc agccgtacag     900
gtcattaaag taacggctgt cactcaccgg aagcatccaa ttatgcaaag tgtgattggg     960
ccatccgaag agcatgtcag catggcagga attcccaccg aagcgagcat cttagaatta    1020
acggatcgcg ctatcccggg taaagtttta aatgtttata atccacctgc aggcggagga    1080
aaactgatga caattatgca gatccataag gatgatgcgg ccgatgaagg tattcagcgg    1140
caagcagcac tgctggcatt tcggcgttc aaagagttga agacagttat tttggtggat    1200
gaagacgttg atattttga tatgaacgat gtaatgtgga ccgtgaatac gcgtttccag    1260
gccgatcagg atttaatgat attaccgggg atgcggaatc acccactgga cccgtcggaa    1320
cgaccagagt atgatctgaa atctattcga acgcgaggca tgtcatcgaa gttggtgatt    1380
gatggcacgg tacccttgga tatgagggaa caatttgaac gcgcgaagtt taagccagtt    1440
gctgactggg aaaaatattt gaaataaaag ggtgatggct gatgaaacgg attgtgattg    1500
gggtgactgg tgcgtccggt acgatttacg cgattgattt gttaaaaaag ttacgggata    1560
agccaggcgt tgaaacacat ttggtaatga gtccgtgggc caccaaaaac ttggcactag    1620
aaacaagtta tacattagcc caagttaaag cgatggccga ctacacgtac agtgatcggg    1680
accaaggggc taagattgct agcggttcat tcctacacga tgggatggtt attgttcccg    1740
ctagcatgaa aacggtggcg ggtgttgcct atgggtttgg cgataatcta attgcgcggg    1800
ctgccgatgt aactattaag gaacatcgac aattgatcat tgtcccacgg gaaacgccac    1860
```

```
tgagtgtgat tcatctagag aatttaacga aactagccaa actaggcgcg caaattattc    1920
cacctattcc cgccttttat aatcagccac aaaccattca agacttagtg gatcatcaga    1980
ctatgaaggt actgggtgca tttggcattc agcaagtgac cgctaagcgt tgggagggag    2040
attag                                                                2045
```

```
<210> SEQ ID NO 23
<211> LENGTH: 38
<212> TYPE: DNA
<213> ORGANISM: Artificial sequence
<220> FEATURE:
<223> OTHER INFORMATION: PCR primer

<400> SEQUENCE: 23
ctctcatatg gtaaatgatc cttatgattt acgaaaag                              38
```

```
<210> SEQ ID NO 24
<211> LENGTH: 28
<212> TYPE: DNA
<213> ORGANISM: Artificial sequence
<220> FEATURE:
<223> OTHER INFORMATION: PCR primer

<400> SEQUENCE: 24
ctctcatatg ctaatctccc tcccaacg                                         28
```

```
<210> SEQ ID NO 25
<211> LENGTH: 630
<212> TYPE: DNA
<213> ORGANISM: Pseudomonas putida

<400> SEQUENCE: 25
atgaacgggc cggaacgcat caccctggcc atgacgggcg cctcgggtgc ccagtatggc      60
cttcgcctgc tcgattgcct ggtacgcgaa gaccgcgagg tgcacttcct gatttccaag    120
gccgcacagt tggtgatggc caccgagacg gatgttgtgt tgccggccaa gccccaggcg    180
atgcaggcct tcctgaccga atacaccggc gcggccgacg gcagatccg tgtgtatggc     240 aaggaagact ggatgtcgcc ggtagcctcg ggttctggcg ccccggcggc aatggtggtg    300 gtccccctgtt ccactggcac cttgtcggcc attgccactg gcgcctgcaa caacctgatc    360
gagcgtgctg ccgacgttac cctcaaggag cgtcgccagc tgatcctggt gccacgcgaa    420
gcgccattct ccaccatcca cctggaaaac atgctcaagc tgtcgcaaat gggcgcggtg    480
atcctgccgg cggcaccggg gttctatcac cagccgcaga ccatcgacga cctggtcgac    540
tttgtcgtgg cgcgtatcct caacctgctg aacatccccc aggatatgtt gccgcgttgg    600
ggcgagcacc acttcggggt ggatgattga                                      630
```

```
<210> SEQ ID NO 26
<211> LENGTH: 23
<212> TYPE: DNA
<213> ORGANISM: Artificial sequence
<220> FEATURE:
<223> OTHER INFORMATION: PCR primer

<400> SEQUENCE: 26
ctctcatatg aacgggccgg aac                                              23
```

```
<210> SEQ ID NO 27
<211> LENGTH: 29
<212> TYPE: DNA
<213> ORGANISM: Artificial sequence
```

<220> FEATURE:
<223> OTHER INFORMATION: PCR primer

<400> SEQUENCE: 27
ctctcatatg tcaatcatcc accccgaag                                29

<210> SEQ ID NO 28
<211> LENGTH: 1574
<212> TYPE: DNA
<213> ORGANISM: Escerichia coli

<400> SEQUENCE: 28
atgtcttccc gcaataatcc ggcgcgtgtc gccatcgtga tggggtccaa aagcgactgg      60
gctaccatgc agttcgccgc cgaaatcttc gaaatcctga atgtcccgca ccacgttgaa     120
gtggtttctg ctcaccgcac ccccgataaa ctgttcagct cgccgaaaag cgccgaagag     180
aacggttatc aggtgattat tgcgggcgca ggcggcgcag cgcatctgcc aggcatgatt     240
gccgccaaaa cgctggtgcc ggtgctgggc gtgccagtac agagcgccgc actgagcggt     300
gtcgatagcc tctactccat cgtacaaatg ccgcgcggca ttccggtggg tacgctggcg     360
attggtaaag ctggcgcggc aaacgcggcg ttactggcag cacaaattct tgcgactcat     420
gataaagaac tgcaccagcg tctgaatgac tggcgcaaag cccagaccga cgaagtgctg     480
gaaaacccgg accgcgagg tgcggcatga acaggtttg cgtcctcggt aacgggcagt       540
taggccgtat gctgcgtcag gcaggcgaac cgttaggcat tgctgtctgg ccagtcgggc     600
tggacgctga accggcggcg gtgcctttc aacaaagcgt gattaccgct gagatagaac      660
gctggccgga aaccgcatta acccgcgagc tggcgcgcca tccggccttt gtgaaccgcg     720
atgtgttccc gattattgct gaccgtctga ctcagaagca gcttttcgat aagctccacc     780
tgccgactgc accgtggcag ttacttgccg aacgcagcga gtggcctgcg gtgtttgatc     840
gtttaggtga gctggcgatt gttaagcgtc gcactggtgg ttatgacggt cgcggtcaat     900
ggcgtttacg cgcaaatgaa accgaacagt taccggcaga gtgttacggc gaatgtattg     960
tcgagcaggg cattaacttc tctggtgaag tgtcgctggt tggcgcgcgc ggctttgatg    1020
gcagcaccgt gttttatccg ctgacgcata acctgcatca ggacggtatt ttgcgcacca    1080
gcgtcgcttt tccgcaggcc aacgcacagc agcaggcgca agccgaagag atgctgtcgg    1140
cgattatgca ggagctgggc tatgtgggcg tgatggcgat ggagtgtttt gtcaccccgc    1200
aaggtctgtt gatcaacgaa ctggcaccgc gtgtgcataa cagcggtcac tggacacaaa    1260
acggtgccag catcagccag tttgagctgc atctgcgggc gattaccgat ctgccgttac    1320
cgcaaccagt ggtgaataat ccgtcggtga tgatcaatct gattggtagc gatgtgaatt    1380
atgactggct gaaactgccg ctggtgcatc tgcactggta cgacaaagaa gtccgtccgg    1440
ggcgtaaagt ggggcatctg aatttgaccg acagcgacac atcgcgtctg actgcgacgc    1500
tggaagcctt aatcccgctg ctgccgccgg aatatgccag cggcgtgatt tgggcgcaga    1560
gtaagttcgg ttaa                                                      1574

<210> SEQ ID NO 29
<211> LENGTH: 28
<212> TYPE: DNA
<213> ORGANISM: Artificial sequence
<220> FEATURE:
<223> OTHER INFORMATION: PCR primer

<400> SEQUENCE: 29

```
ctctcatatg tcttcccgca ataatccg                                          28
```

<210> SEQ ID NO 30
<211> LENGTH: 31
<212> TYPE: DNA
<213> ORGANISM: Artificial sequence
<220> FEATURE:
<223> OTHER INFORMATION: PCR primer

<400> SEQUENCE: 30

```
ctctcatatg ttaaccgaac ttactctgcg c                                      31
```

<210> SEQ ID NO 31
<211> LENGTH: 1716
<212> TYPE: DNA
<213> ORGANISM: Saccharomyces cerevisiae

<400> SEQUENCE: 31

```
atggattcta gaacagttgg tatattagga gggggacaat tgggacgtat gattgttgag        60
gcagcaaaca ggctcaacat taagacggta atactagatg ctgaaaattc tcctgccaaa      120
caaataagca actccaatga ccacgttaat ggctcctttt ccaatcctct tgatatcgaa      180
aaactagctg aaaaatgtga tgtgctaacg attgagattg agcatgttga tgttcctaca      240
ctaaagaatc ttcaagtaaa acatcccaaa ttaaaaattt acccttctcc agaaacaatc      300
ggattgatac aagacaaata tattcaaaaa gagcatttaa tcaaaaatgg tatagcagtt      360
acccaaagtg ttcctgtgga acaagccagt gagacgtccc tattgaatgt tggaagagat      420
ttgggttttc cattcgtctt gaaatcgagg actttggcat acgatggaag aggtaacttc      480
gttgtaaaga taaggaaat gattccggaa gctttggaag tactgaagga tcgtcctttg      540
tacgccgaaa atgggcacc atttactaaa gaattagcag tcatgattgt gagatctgtt      600
aacggtttag tgttttctta cccaattgta gagactatcc acaaggacaa tatttgtgac      660
ttatgttatg cgcctgctag agttccggac tccgttcaac ttaaggcgaa gttgttggca      720
gaaaatgcaa tcaaatcttt tcccggttgt ggtatatttg gtgtggaaat gttctatttta     780
gaaacagggg aattgcttat taacgaaatt gccccaaggc ctcacaactc tggacattat      840
accattgatg cttgcgtcac ttctcaattt gaagctcatt tgagatcaat attggatttg      900
ccaatgccaa agaatttcac atctttctcc accattacaa cgaacgccat tatgctaaat      960
gttcttggag acaaacatac aaaagataaa gagctagaaa cttgcgaaag agcattggcg     1020
actccaggtt cctcagtgta cttatatgga aaagagtcta gacctaacag aaaagtaggt     1080
cacataaata ttattgcctc cagtatggcg gaatgtgaac aaaggcttaa ctacattaca     1140
ggtagaactg atattccaat caaaatctct gtcgctcaaa agttggactt ggaagcaatg     1200
gtcaaaccat tggttggaat catcatggga tcagactctg acttgccggt aatgtctgcc     1260
gcatgtgcgg ttttaaaaga ttttggcgtt ccatttgaag tgacaatagt ctctgctcat     1320
agaactccac ataggatgtc agcatatgct atttccgcaa gcaagcgtgg aattaaaaca     1380
attatcgctg gagctggtgg ggctgctcac ttgccaggta tggtggctgc aatgacacca     1440
cttcctgtca tcggtgtgcc cgtaaaaggt tcttgtctag atggagtaga ttctttacat     1500
tcaattgtgc aaatgcctag aggtgttcca gtagctaccg tcgctattaa taatagtacg     1560
aacgctgcgc tgttggctgt cagactgctt ggcgcttatg attcaagtta tacaacaaaa     1620
atggaacagt ttttattgaa gcaagaagaa gaagttcttg tcaaagcaca aaagttagaa     1680
actgtcggtt acgaagctta tctagaaaac aagtaa                               1716
```

<210> SEQ ID NO 32
<211> LENGTH: 34
<212> TYPE: DNA
<213> ORGANISM: Artificial sequence
<220> FEATURE:
<223> OTHER INFORMATION: PCR primer

<400> SEQUENCE: 32
ctctccatgg attctagaac agttggtata ttag        34

<210> SEQ ID NO 33
<211> LENGTH: 39
<212> TYPE: DNA
<213> ORGANISM: Artificial sequence
<220> FEATURE:
<223> OTHER INFORMATION: PCR primer

<400> SEQUENCE: 33
ctctccatgg ttacttgttt tctagataag cttcgtaac        39

<210> SEQ ID NO 34
<211> LENGTH: 2252
<212> TYPE: DNA
<213> ORGANISM: Enterobacter cloacae

<400> SEQUENCE: 34
atgagattga tcgtgggaat gacgggagca acaggtgctc cgctgggtgt ggctttactg        60
caggcgttac gtgacatgcc agaggttgaa acccatctgg tgatgtcgaa atgggcgaaa       120
accaccattg agctggaaac gccttatacc gcgcaggatg tcgccgccct ggcagatgtc       180
gttcacagtc ctgccgatca ggctgccacc atctcctccg gctcgtttcg taccgacggc       240
atgatcgtca ttccctgcag catgaaaacg ctggcgggta ccgcgcgggg ctatgccgaa       300
gggctggtgg ccgtgcggc agacgtggtg ctgaaagagg ggcgcaagct ggtgctggtc       360
ccgcgtgaaa cgccgctcag caccattcat ctggagaaca tgctcgcgct ttcccgcatg       420
ggggtggcga tggtgccgcc catgcctgcg tattacaacc cccgcaaac cgccgatgat       480 atcacccagc atatcgtgac ccgcgtactc gaccagtttg gtctggagca caaaaaggcg       540
cgtcgctgga acggcctgca ggcggcgaaa catttttcac aggagaataa cgatggcatt       600
tgatgatttg agaagcttcc tgcaggcgct agatgagcaa gggcaactgc tgaaaattga       660
agaagaggtc aatgcggagc cggatctggc ggcggccgct aacgcgacgg gacgtatcgg       720
tgatggtgcg cctgcgctgt ggttcgataa cattcgcggg tttaccgatg ccagggtggt       780
gatgaacacc atcggctcct ggcagaacca cgccatttcg atgggctgc ggcgaatac       840 cccggtcaaa aagcagatcg atgagtttat tcgccgctgg gataaattcc cggtcgcacc       900
ggagcgccgg gccaaccccg catgggcgca gaatacggtg acggtgagg agattaacct       960 gttcgacatc ctgccgctgt ttcgcctgaa cgacggggac ggcggttttt atctcgacaa      1020
agcgtgcgtt gtctcgcgcg atccgctcga cccggaccat ttcggcaagc agaacgtcgg      1080
tatttaccgc atggaagtga agggcaaacg taagctcggc ctgcagccgg tgccgatgca      1140
tgatatcgcc ctgcatctgc ataaagccga agagcgtggt gaagacctgc cgattgcgat      1200
tacgttgggc aacgatccga tcatcacccct gatgggcgca acgccgctga aatacgatca      1260
gtccgagtat gaaatggccg gggcgctgcg tgaaagcccg tacccgattg cgaccgcgcc      1320
gttgaccggc ttcgatgtgc cgtggggtc tgaagtgatc ctggaagggg tgattgaagg      1380

```
ccgtaaacgt gaaattgaag ggccgttcgg tgagtttacc gggcactatt cgggcggacg    1440
caatatgacg gtggtccgta ttgataaagt ctcgtaccgc accaaaccga ttttcgaatc    1500
cctctatctc gggatgccct ggaccgagat cgactacctg atggggccag ccacctgtgt    1560
gccgctttac cagcaactga aagcggagtt ccctgaagtg caggcggtga acgcgatgta    1620
tacccacggt ctgctggcga tcatctccac caaaaaacgc tacggtggtt ttgcccgcgc    1680
ggtcggttta cgcgccatga ccacgccgca tggcctgggc tatgtgaaga tggtgattat    1740
ggtggatgaa gatgtcgatc cgttcaacct gccgcaggtg atgtgggcgc tgtcatcaaa    1800
agtgaacccg gcaggggatc tggtgcagct gccgaacatg tcggttcttg agcttgatcc    1860
tgggtccagc ccggcaggca tcaccgacaa gctgattatt gatgccacca cgcctgttgc    1920
gccggataac cgcggtcact acagccagcc ggtgcaggat ttacctgaaa ccaaagcctg    1980
ggctgaaaag ctgactgcga tgctggcagc acgccaataa ggaggaaaag atgatttgtc    2040
cacgttgtgc cgatgagcaa attgaggtga tggccacatc accggtgaaa gggatctgga    2100
cggtttatca gtgccagcat tgcctgtata cctggcgcga tactgagccg ctgcgtcgta    2160
ccagccgcga acattaccct gaagcgttcc gcatgacgca aaggatatt gatgaggcgc    2220 cgcaggtacc gaccattccg ccattgctgt aa                                  2252

<210> SEQ ID NO 35
<211> LENGTH: 30
<212> TYPE: DNA
<213> ORGANISM: Artificial sequence
<220> FEATURE:
<223> OTHER INFORMATION: PCR primer

<400> SEQUENCE: 35
ctctcatatg agattgatcg tgggaatgac                                       30

<210> SEQ ID NO 36
<211> LENGTH: 30
<212> TYPE: DNA
<213> ORGANISM: Artificial sequence
<220> FEATURE:
<223> OTHER INFORMATION: PCR primer

<400> SEQUENCE: 36
ctctcatatg ttacagcaat ggcggaatgg                                       30
```